(12) United States Patent
Dandurand

(10) Patent No.: US 7,485,885 B2
(45) Date of Patent: Feb. 3, 2009

(54) ELECTROMAGNETIC RADIATION TRANSFORMATION FOR POWERED DEVICES

(76) Inventor: Kim Dandurand, 560 W. Canfield Ave., Ste 400, Coeur d'Alene, ID (US) 83815

( * ) Notice: Subject to any disclaimer, the term of this patent is extended or adjusted under 35 U.S.C. 154(b) by 0 days.

(21) Appl. No.: 11/781,899

(22) Filed: Jul. 23, 2007

(65) Prior Publication Data

US 2008/0048136 A1 Feb. 28, 2008

Related U.S. Application Data

(60) Provisional application No. 60/820,205, filed on Jul. 24, 2006.

(51) Int. Cl.
*G21F 3/00* (2006.01)
*G21F 1/00* (2006.01)
*G21K 1/093* (2006.01)
(52) U.S. Cl. .............. 250/515.1; 250/503.1; 250/505.1; 455/117
(58) Field of Classification Search .............. 250/515.1, 250/503.1, 505.1; 455/117
See application file for complete search history.

(56) References Cited

U.S. PATENT DOCUMENTS

| 5,449,376 | A | 9/1995 | Callahan |
| 2002/0125419 | A1 | 9/2002 | Callahan |
| 2008/0017812 | A1* | 1/2008 | Dandurand .............. 250/503.1 |
| 2008/0020722 | A1* | 1/2008 | Dandurand .................. 455/117 |
| 2008/0050325 | A1* | 2/2008 | Dandurand ................... 424/64 |
| 2008/0061253 | A1* | 3/2008 | Dandurand .............. 250/515.1 |

* cited by examiner

*Primary Examiner*—Nikita Wells

(57) ABSTRACT

Electromagnetic radiation transformation for powered devices is described. In embodiment(s), a wireless phone (e.g., a cellular phone) includes one or more sources that emit electromagnetic radiation, such as an internal power supply or antenna system of the wireless phone. The wireless phone can also include a paramagnetic material in a quantity sufficient to counteract the electromagnetic radiation emitted by the source. To counteract harmful effects of the electromagnetic radiation, the paramagnetic material can transform the electromagnetic radiation, such as to effectuate a frequency transformation and/or to alter an intensity of the electromagnetic radiation.

43 Claims, 14 Drawing Sheets

ELECTROMAGNETIC RADIATION TRANSFORMATION FOR POWERED DEVICES

RELATED APPLICATION

This application claims priority from U.S. Provisional Application Ser. No. 60/820,205 filed Jul. 24, 2006 entitled "EMF Radiation Neutralizer" to Dandurand, the disclosure of which is incorporated by reference herein in its entirety.

BACKGROUND

Electromagnetic radiation can include any form of electromagnetic frequencies (e.g., radio frequencies), electromagnetic interference or fields, and/or electro-pollution all which may be commonly referred to as "EMF" or "EMF radiation". Electromagnetic radiation may originate from a variety of sources, including devices that are encountered during typical everyday life, such as wireless phones, music players, microwave ovens, computer devices, and so on. Consequently, exposure by a typical person to EMF radiation continues to increase as the prevalence of these devices also continues to increase. For example, it was not long ago that wireless phones (e.g., cellular phones) were rarely encountered. However, the use of wireless phones has become so pervasive that many users even forgo traditional wired phones in their homes for the convenience of wireless phones, even by children.

The continued and ever increasing exposure to EMF radiation may have detrimental effects to users that are exposed to EMF radiation emitted from devices and/or to those that simply encounter EMF radiation during a typical day. Electromagnetic radiation in the form of x-rays, ultraviolet, and microwaves, as well as other portions of the electromagnetic spectrum such as radio-frequency waves emitted from cellular phones, computers, televisions, and other devices are known to damage the human body. For instance, it has been identified herein that EMF radiation may cause damage to Deoxyribonucleic Acid (DNA), and that human DNA reacts adversely to incoherent manmade electromagnetic fields emanating from a cellular phone.

Additionally, as the understanding of EMF radiation and the detrimental effects continues to develop, it is quite possible that a variety of other detrimental effects from exposure to EMF radiation may also be found. Further, this damage may be exacerbated depending on how the EMF radiation is encountered. For example, use of a wireless phone held against the ear may increase EMF radiation and damage sensitive areas of the brain. A variety of other instances may also be encountered.

Research has been focused on the health hazards of cell phones due to their endemic use. Some of the studies that measure the biological effects of actual, broad spectrum cell phone radiation (not isolated or simulated components) show detrimental effects. Reports that have been asserted to counter these studies are asserted by some to be biased in experimental design to favor conditions that are expected to result in no radiation effects. For example, it was asserted most studies use single isolated frequencies claimed to be emitted from cell phones. However, these individual frequencies are not representative of the broader spectrum of frequencies actually emitted by cell phones. In addition, the questionable experiments often use low radiation doses, referred to as specific absorption rates (SAR). These studies that are designed to result in no biological damage use EMF radiation doses as low as 0.08 W/kg, whereas experiments designed to show biological damage would use EMF radiation doses as high as 100 W/kg.

As previously observed with video display monitors, the biological effects of electromagnetic radiation are ascertainable when resonance conditions are met. It is now well established that many confounding variables (e.g., the strength and orientation of the geomagnetic field) can create experimental conditions where biological effects are not observed. Thus, studies that fail to measure biological effects from cell phone radiation or from other sources of EMF may not have obtained the resonance conditions which when met cause these effects. Therefore, it has been suggested that the focus on studies which show no effects and conclude that cell phone radiation is safe depart from the fact that in real-life, cell phone users are exposed to this radiation numerous times during the course of a day and over the course of several years. Most scientific studies do not take into account the chronic use of cell phones.

In some cases the bimolecular sensors that resonate with harmful radiation is known. Unfortunately, the most fundamental molecule in the body, DNA itself, can act as a target for such radiation even when it is non-ionizing and low-level. Studies have concluded that radio-frequency EMF from cell phones, at intensities similar to those emitted from contemporary cell phones, directly damage DNA. This is the same type of damage that was previously established from exposure to UV and X-rays. Previous research with other types of EMF, not necessarily emitted by cell phones, indicated shape (conformation) changes in DNA. Strands of DNA break or conformational changes in the DNA can result in the formation of damaged proteins in a body.

As devices and other sources that emit EMF radiation become increasingly prevalent in our everyday lives, so too does the likelihood of exposure by users of the devices and others that simply encounter harmful EMF radiation. Indeed, in current times it may be difficult if not nearly impossible for users to avoid this exposure, such as through use of a microwave, interaction with a personal computer, viewing of a traditional television, listening to a portable music player, using of a handheld video game, and so on.

SUMMARY

This summary is provided to introduce simplified concepts of electromagnetic radiation transformation for powered devices. The simplified concepts are further described below in the Detailed Description. This summary is not intended to identify essential features of the claimed subject matter, nor is it intended for use in determining the scope of the claimed subject matter.

In embodiment(s) of electromagnetic radiation transformation for powered devices, a wireless phone (e.g., a cellular phone) includes one or more sources that emit electromagnetic radiation, such as an internal power supply or antenna system of the wireless phone. The wireless phone can also include a paramagnetic material in a quantity sufficient to counteract the electromagnetic radiation emitted by the source. To counteract harmful effects of the electromagnetic radiation, the paramagnetic material can transform the electromagnetic radiation, such as to effectuate a frequency transformation and/or to alter an intensity or waveform of the electromagnetic radiation.

In other embodiment(s) of electromagnetic radiation transformation for powered devices, a casing that supports the components of the wireless phone can include the paramagnetic material which counteracts the electromagnetic radiation emitted by the components of the wireless phone. In another embodiment, the paramagnetic material is formed in a disk-shaped, layered product that includes an outer layer, one or more layers of the paramagnetic material, and an adhesive layer that adheres to the wireless phone. The layers of the paramagnetic material can include a base material, such as an ink-based material or a silica-based material, to support the paramagnetic material. The disk-shaped, layered product can also include a bonding agent that bonds the layers of the paramagnetic material between the outer layer and the adhesive layer.

BRIEF DESCRIPTION OF THE DRAWINGS

Embodiments of electromagnetic radiation transformation are described with reference to the following drawings. The same numbers are used throughout the drawings to reference like features and components.

DETAILED DESCRIPTION

Overview

Figure 1:
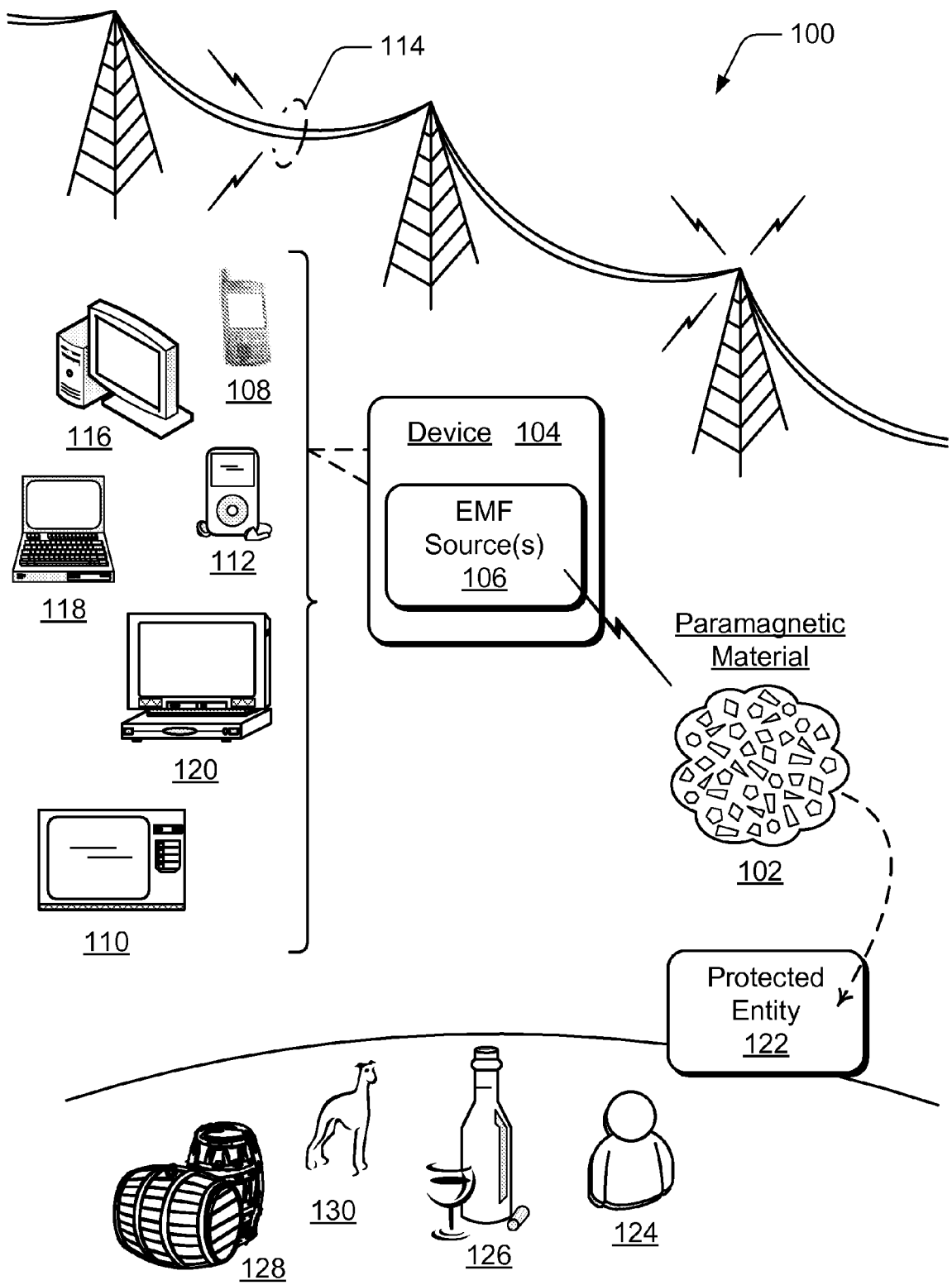
FIG. 1 illustrates an example environment in which embodiments of electromagnetic radiation transformation can be implemented.

Electromagnetic radiation may originate from a variety of sources, including devices that are encountered during typical everyday life, such as wireless phones, music players, microwave ovens, computer devices, and so on. Consequently, exposure by a typical person to EMF radiation continues to increase as the prevalence of these devices also continues to increase. The understanding of the consequences to exposure to EMF radiation, however, continues to develop. For example, studies have shown that analysis of the harmful effects of a single frequency on a biological organism may be inconclusive when compared to cumulative effects of multiple frequencies and different intensities on the organism. A variety of other examples are also available as further detailed below.

Accordingly, techniques are described herein that may be used to counteract the possible harmful effects of EMF radiation as well as provide other benefits, such as to provide protection against heavy metals. One or more such techniques involve the use of paramagnetic materials which are substances having a magnetic susceptibility greater than zero (e.g., substances that are drawn into a magnetic field). For example, paramagnetism may be used to describe a tendency of atomic magnetic dipoles, due to quantum-mechanical spin as well as electron orbital angular momentum, to align with an external magnetic field. Paramagnetic materials attract and repel like normal magnets when subject to a magnetic field. This alignment of the atomic dipoles with the magnetic field tends to strengthen it, and is described by a relative magnetic permeability greater than unity or, equivalently, a relatively small positive magnetic susceptibility. For example, certain iron bearing minerals may exhibit paramagnetism which causes them to be weakly attracted to magnetic fields.

Diamagnetism is a form of magnetism that is exhibited by a substance in the presence of an externally applied magnetic field. It is the result of changes in the orbital motion of electrons. All materials show a diamagnetic response in an applied magnetic field; however for materials which show some other form of magnetism (such as ferromagnetism or paramagnetism), the diamagnetism is completely overpowered. Substances which only, or mostly, display diamagnetic behavior are termed diamagnetic materials, or diamagnets. Materials that are said to be diamagnetic are those which are usually considered by non-physicists as "non-magnetic", and include water, DNA, most organic compounds such as petroleum and some plastics, and many metals such as mercury, gold, and bismuth.

Many common materials such as water, wood, plants, animals, diamonds, fingers, and so on are usually considered to be non-magnetic but in fact, they are very weakly diamagnetic. Diamagnets repel, and are repelled by a strong magnetic field. The electrons in a diamagnetic material rearrange their orbits slightly creating small persistent currents which oppose the external magnetic field. Two of the strongest diamagnetic materials are graphite and bismuth. Even paramagnetic compounds (having unpaired electrons) will also have a smaller, diamagnetic contribution to their magnetism if there are electron pairs present.

Accordingly, embodiments of electromagnetic radiation transformation includes devices, systems, and/or procedures that may utilize paramagnetic and/or diamagnetic techniques to transform electromagnetic frequencies (e.g., radio frequencies), electromagnetic interference or fields, and/or electro-pollution all which may be commonly referred to as electromagnetic radiation, "EMF", or "EMF radiation". An example of such a material which has paramagnetic properties (one of which is electromagnetic radiation transformation) is known as an "Aulterra Rock", "Aulterra Powder", or "Aulterra Neutralizer". To counteract harmful effects of electromagnetic radiation, the paramagnetic material can transform electromagnetic radiation, such as to effectuate a frequency transformation and/or to alter an intensity or waveform of the electromagnetic radiation.

Although "Aulterra Rock", "Aulterra Powder", and/or "Aulterra Neutralizer" are given as examples in the following discussion, it should be readily apparent that this discussion is not limited to the "Aulterra Rock", "Aulterra Powder", or "Aulterra Neutralizer" as other substances having similar properties are also contemplated. In various embodiments, the paramagnetic material referred to herein typically has a paramagnetic intensity or value of approximately 400 and above which can be embodied to effectuate electromagnetic radiation transformation. Any one or combination of the "Aulterra Rock", "Aulterra Powder", and/or "Aulterra Neutralizer", however, typically resonates with an approximate paramagnetic value of 3,000 and above, and in various embodiments, the paramagnetic material referred to herein has a paramagnetic value in a range between 3,000 and 6,000.

Paramagnetic material may be used in a variety of ways to effectuate electromagnetic radiation transformation. For example, the paramagnetic material may be provided in a quantity sufficient to counteract electromagnetic radiation emitted by a device, such as a cell phone, music player, microwave oven, and so on. Counteraction of electromagnetic radiation may be performed in a variety of ways, such as through emission of an electromagnetic field, altering of a waveform, and so on, further discussion of which may be found in relation to FIGS. 1-3 and the studies described below.

In one or more additional embodiments, techniques for electromagnetic radiation transformation can be implemented for powered devices, such as cell phones. For example, a wireless phone, such as a cordless phone, cellular phone, or other similar device includes one or more sources that emit electromagnetic radiation, such as an internal power supply or antenna system. The wireless phone can also include paramagnetic material in a quantity sufficient to counteract the electromagnetic radiation emitted by the source(s). To counteract harmful effects of the electromagnetic radiation, the paramagnetic material can transform the electromagnetic radiation, such as to effectuate a frequency transformation and/or to alter an intensity or waveform of the electromagnetic radiation.

In one or more additional embodiments, techniques for electromagnetic radiation transformation can be implemented for therapeutic techniques with paramagnetic material. For example, devices such as jewelry, pillows, soil additives, labels, containers and so on may incorporate paramagnetic material to effect a therapeutic result. In an example of a wine, for instance, a label or container for the wine has been shown to increase a shelf life of the wine when it includes a quantity of paramagnetic material. A variety of other examples are also contemplated, such as protection against heavy metal toxicity, exposure to electromagnetic fields, and so on, further discussion of which may be found in relation to the following figures.

In one or more additional embodiments, techniques for electromagnetic radiation transformation can be implemented for cosmetic composition(s) with paramagnetic material. For example, cosmetics may be configured to implement the therapeutic techniques described above to a wearer of the cosmetic, such as to protect a user against outside influences as well as promote therapeutic response from inside influences, further discussion of which may be found in relation to the corresponding section.

In one or more additional embodiments, techniques for electromagnetic radiation transformation can be implemented for power transports. For example, a power conducting system can include a power transport such as a conduit, power line, electrical cord, and the like that conducts power which is a source of electromagnetic radiation. The power conducting system can also include a paramagnetic material in a quantity sufficient to counteract the electromagnetic radiation emitted by the source. In an embodiment, the power transport can be covered by a coating and/or an insulation cover that includes the paramagnetic material. To counteract harmful effects of the electromagnetic radiation, the paramagnetic material can transform the electromagnetic radiation, such as to effectuate a frequency transformation and/or to alter an intensity or waveform of the electromagnetic radiation.

In the following discussion, a general description of electromagnetic radiation transformation techniques is first provided along with studies that support these techniques. Exemplary embodiments are then described of electromagnetic radiation transformation techniques. Although these exemplary embodiments are provided as examples of electromagnetic radiation transformation techniques, it should be readily apparent that the techniques may be employed in a variety of other ways. For example, the paramagnetic techniques may also be employed to reduce harmful effects of heavy metals and for other therapeutic purposes.

While features and concepts of the described systems and procedures for electromagnetic radiation transformation can be implemented in any number of different environments and/or systems, embodiments and techniques of electromagnetic radiation transformation are described in the context of the following example systems and environments.

Electromagnetic Radiation Transformation

FIG. 1 depicts an example environment 100 in which various embodiments of paramagnetic techniques can be employed. The environment 100 is shown with a quantity of paramagnetic material 102 that may be configured for a variety of uses and effects. For example, the paramagnetic material 102 may be configured for use with a device 104 to transform electromagnetic radiation emitted by the device 104, which is illustrated as an EMF source 106 in FIG. 1. The device 104 may assume a wide variety of configurations, such as a cell phone 108, microwave oven 110, music player 112 and "other" devices, such as power conduits 114, personal 116 and laptop 118 computers, a television 120, and so on as depicted in FIG. 1. In this example the paramagnetic material 102 is configured to transform electromagnetic radiation that is emitted "from" the device 104.

The paramagnetic material 102 may also be configured to protect an entity 122 from "outside" electromagnetic influences that emit electromagnetic radiation. For example, the paramagnetic material 102 may be configured to protect cell phone 108, microwave 110, music player 112 and "other" devices from electromagnetic radiation emitted from other devices. A personal computer (PC), for instance, may be installed in a "noisy" environment having a relatively high amount of electromagnetic radiation that adversely affects operation of the personal computer. By providing the personal computer with the paramagnetic material 102, however, the personal computer may experience normal operation through transformation of the electromagnetic radiation by the paramagnetic material.

The paramagnetic material 102 may also be employed to protect a variety of other entities 122 that are not devices, such as a person 124 (i.e., a human being), a perishable product (e.g., wine 126 or other liquids 128), a pet 130 (e.g., dog, cat, bird, and so on) or other biological entity, and other entities. Mechanisms that may be employed to provide this transformation to internal and/or external electromagnetic radiation are further described below.

In the following studies, one technique that has been asserted is a phenomenon in biological systems referred to as macroscopic quantum coherence. This mechanism includes an assertion that the energy radiating from paramagnetic material 102 may be highly coherent (e.g., laser-like) which may be activated during manufacture of the paramagnetic material 102 to make the intrinsic energy of the paramagnetic material 102 coherent. The paramagnetic material 102 may also have intrinsic quantum properties similar to other complex lattice structures which also exhibit quantum properties.

Another technique that has been proposed in a study discussed below is a "bio-protective effect" which reduces the intensity of offending electromagnetic radiation. At least two different mechanisms may be employed for such a technique, such as a biochemical defense response and a physical alteration of encountered electromagnetic radiation.

A further technique involves a magneto resistance response (e.g., Meissner effect), which is induced when the paramagnetic material 102 is in the presence of magnetic fields. Thus, paramagnetic shielding (in addition to ferromagnetic shielding) is one explanation for the ability of the paramagnetic material 102 to reverse effects of cell phone radiation, such as on DNA renaturation. Ferromagnetic transduction has been previously proposed to mediate biological effects of electromagnetic radiation (e.g., from cell phones) because of their resonance with the biological mineral magnetite. Furthermore, the fact that the Meissner effect is dependent on magnetic field orientation can also explain off-resonance conditions and why individual experiments are not reproducible in each case, but are reproducible as a whole.

Yet another technique involves emission by the paramagnetic material 102 of an electromagnetic field that counteracts electromagnetic fields encountered within that field. This observation provides another mechanism to explain how the paramagnetic material 102 may cancel detrimental effects of electromagnetic radiation, since it is known that adding coherent information to a classical EMF modifies its ability to influence biological systems. For example, the paramagnetic material may both generate magnetic fields (due to the presence of unpaired electrons) and absorb magnetic fields (a property called magnetic susceptibility). Thus, it is likely that the paramagnetic material 102 also generates a classical EMF which can couple to and counteract another electromagnetic field, such as to neutralize harmful effects to the "other" electromagnetic field. Electromagnetic field emission by the paramagnetic material 102 may also be used to explain the effect of the paramagnetic material to counteract detrimental effects of heavy metals on biological specimens (e.g., DNA). Further discussion of these techniques may be found in relation to the studies which follow the subsequent exemplary procedures. A variety of other techniques are also contemplated, such as by altering a waveform of electromagnetic radiation encountered by the paramagnetic material 102.

Figure 2:
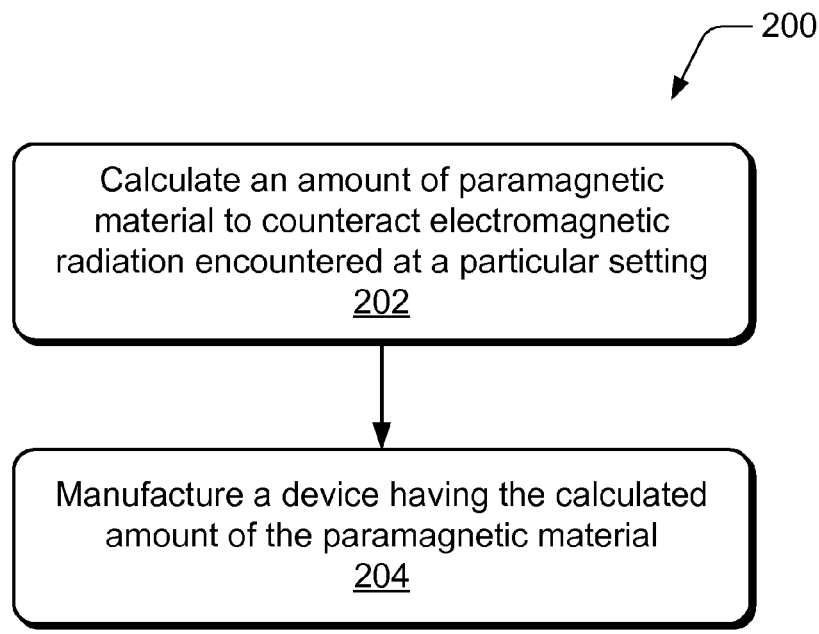
FIG. 2 illustrates example procedure(s) for electromagnetic radiation transformation in accordance with one or more embodiments.

FIG. 2 depicts example procedure(s) 200 of electromagnetic radiation transformation, and describes techniques that may be implemented utilizing the previously described environment, or any other environment and/or system described herein. The procedure is shown as a set of blocks and described in an order that is not intended to be construed as a limitation. Any number of the described blocks can be combined in any order to implement the procedure, or an alternate procedure. In this example, reference is made to environment 100 shown in FIG. 1.

Procedure 200 illustrates an example implementation in which a device is manufactured that has an amount of paramagnetic material which is calculated to counteract electromagnetic radiation to be encountered at a particular setting. An amount of paramagnetic material is calculated to counteract electromagnetic radiation to be encountered at a particular setting (block 202). For example, a magnetometer may be used to measure the overall intensity of electromagnetic radiation across one or more desired ranges of frequencies of the electromagnetic spectrum. Differing amounts of paramagnetic material may then be disposed within an effective range of the emitting devices (in this instance the cell phone) and measurements may then be made using the magnetometer. This process may be repeated until a desired effect is encountered, which in this instance is a decrease in intensity of the electromagnetic radiation for particular frequencies (e.g., ranges of frequencies) emitted by the emitting device (e.g., the cell phone), such as a decrease of thirty-five (35) percent, fifty (50) percent, seventy (70) percent, and so on. In addition to a decrease in intensity of electromagnetic radiation, a variety of other effects are also contemplated, such as to reduce harmful effects of heavy metals, effect of EMF on DNA, and so forth.

A device is then manufactured having the calculated amount of the paramagnetic material (block 204). For example, the device may be configured as a disk that is to be disposed within or on the cell phone of the previous example. The device that includes the paramagnetic material may also assume a variety of other configurations, such as a coating (e.g., paint), jewelry, a cosmetic, a product label or container, and so on, further discussion of which may be found in relation to the following sections.

Figure 3:
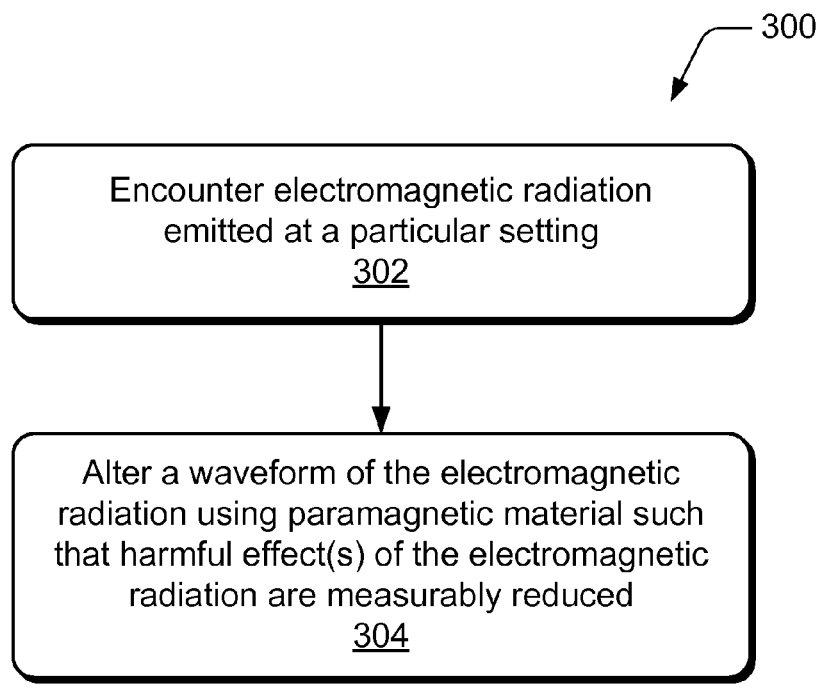
FIG. 3 illustrates example procedure(s) for electromagnetic radiation transformation in accordance with one or more embodiments.

FIG. 3 depicts example procedure(s) 300 of electromagnetic radiation transformation, and describes techniques that may be implemented utilizing the previously described environment, or any other environment and/or system described herein. The procedure is shown as a set of blocks and described in an order that is not intended to be construed as a limitation. Any number of the described blocks can be combined in any order to implement the procedure, or an alternate procedure. In this example, reference is made to environment 100 shown in FIG. 1.

Procedure 300 illustrates an example implementation in which harmful effects of electromagnetic radiation are reduced by altering a waveform of the electromagnetic radiation using a paramagnetic material. Electromagnetic radiation is encountered that is emitted at a particular setting (block 302). For example, a cell phone may emit electromagnetic radiation from an internal antenna or power source, a human being may emit electromagnetic radiation, a wine bottle may encounter electromagnetic radiation in a storage setting, and so on.

A waveform of electromagnetic radiation is altered using a paramagnetic material such that one or more harmful effects of the encountered electromagnetic radiation are measurably reduced (block 304). The waveform of electromagnetic radiation may be altered, for example, such that an incoherent waveform is transformed into a coherent waveform through interaction with the paramagnetic material. The reduction in the harmful effects may be measurably reduced in a variety of ways, such as by examination of DNA rewinding, intensity of electromagnetic radiation at particular frequencies known or suspected to cause harmful effects, and so on. Further discussion of measurement and reduction of harmful effects may be found in relation to the following studies.

Conformational Changes in Human DNA Characterize the Radiated Energy from the Aulterra Formulation Information content associated with both classical and non-classical (subtle, non-Hertzian, scalar) electromagnetic energy can be stored in physical objects. These objects include water, geometric patterns, electronic circuits, and even paper. For water and electronic circuits, preliminary evidence suggests that the stored information can be subsequently retrieved or utilized by biological systems, thereby producing a biological effect. In this sense these objects have a memory of the information stored within them. Although longtime storage of information in physical objects is considered an anomaly in the eyes of traditional science, it has been demonstrated experimentally.

Research by Glen Rein, Ph.D. in this area has demonstrated that subtle energy generated from "free energy" devices and those associated with human intention can be stored in water for several months if the optical properties of water are measured using a special form of ultraviolet (UV) spectroscopy. Furthermore, the stored energy is biologically active when the water is exposed to a variety of biological systems. One of the biological targets used in these studies was the DNA molecule. In addition to these responses to stored or imprinted energy, DNA has been shown to act as an antenna for other forms of subtle energy. Thus, it has been discovered that in addition to classical EM fields, subtle energy resonates with the DNA molecule and may cause physical changes in its secondary structure (e.g., winding and unwinding of the helix).

DNA Exposed to the Energy of Aulterra Powder

The recovery curve is a typical curve when DNA is suspended in water and left to spontaneously rewind. When the DNA was placed on the Aulterra Powder for one day and then measured, there was no change in the recovery curve. However, after 3, 4, or 5 days of exposure to the energy from the powder, a rather interesting recovery curve is obtained.

Instead of a smooth and gradual rewinding process, the recovery curve is oscillatory in nature. This means that the DNA rewinds, then unwinds a little, then continues to rewind and continues to go through cycles of winding and unwinding. This oscillatory behavior has been observed in other systems. It is interesting to note that in the case of experiments performed by others, it was proposed that the observed oscillatory behavior of water in those experiments was induced by human intention associated with healing states of consciousness. Healing states of consciousness have a proposed association with coherent oscillatory EEG patterns. Furthermore, it was demonstrated that the energy from healers could affect conformation of DNA when the electrical activity of their EEG exhibited such oscillatory behavior. Thus, by inference the energy emitted from the Aulterra Powder may be similar to the energies associated with healers.

Neutralizing the Effects of Heavy Metal Toxicity

Copper (Cu(II)) was chosen as a representative heavy metal because the biological action of copper is mediated by binding to DNA and causing it to unwind. A series of experiments were performed to determine the appropriate concentration of copper, i.e., a high enough concentration that would produce a measurable effect on DNA but not too high as to totally overload the system. It was predicted that the ability of the energy from Aulterra's Powder to neutralize the toxic effect of copper would be minimized at higher concentrations of copper. Based on the literature, a concentration of 1 mM was initially tested. In order to determine the effect of copper, the slope of the recovery curves was analyzed first in the absence of any heavy metals. The normal recovery rate was determined in six separate experiments with the average value for the slope of $-0.813$: f: $0.06$. The recovery rate was then measured in four separate experiments when DNA was exposed to 1 mM copper for 2 days. The average slope was dramatically reduced to $0.023$: f: $0.015$.

Preliminary experiments were conducted to determine whether this large effect of copper on DNA recovery rates could be neutralized if the DNA was placed on top of the Aulterra powder while being exposed to the copper. After two days, the average slope was $-0.011$, which is not much different than $-0.023$ (both giving around 98% inhibition) indicating that the energy from the Aulterra powder did not neutralize the damaging effect of the copper. However, after three days the slope was $-0.28$ (66% inhibition) and after four days the slope was $-0.36$ (55% inhibition), rapidly approaching the $-0.81$ values for the slope in the absence of copper. These results demonstrate that the energy from the Aulterra powder does in fact counteract, and in this instance partially neutralize the toxic effect of copper by reducing the 97% inhibition (with no energy) to 55% in the presence of the powder. The effect appears to be linear with time indicating that the longer the DNA was exposed to the energy, the larger the neutralizing ability. The results were encouraging, but revealed partial protection from copper when used at 1 mM concentrations.

It is possible that only partial protection occurred because the concentration of the toxin was too high. Therefore, these experiments were repeated with a lower dose of copper, 0.5 mM. Based on the previous experiments, it was predicted that a neutralizing effect of the low concentration of copper would be seen after only two days. Therefore, twelve separate experiments were done with DNA exposed to 0.5 mM copper in the presence and absence of energy from Aulterra's Powder. See Table 1 which includes the raw data from six (6) separate experiments showing R2 slope values for slope calculated buy computer. In this case the copper alone caused an 86% inhibition of DNA recovery, giving an average slope value of $-0.11$: 1 $0.25$. In the presence of the energy from the Aulterra Powder, this effect was reduced to only 36%, giving an average slope of $-0.52$: 1 $0.18$. The raw data from each of the twelve (12) separate experiments is shown in Table 1. Statistical comparison of the last two numbers reveals a highly significant difference (p=0.01). The results, taken together with the previous results using higher concentrations of copper (Table 2), clearly demonstrate the ability of the energy from Aulterra's powder to neutralize the toxic effect of copper. Table 2 indicates an effect of the energy from Aulterra's Powder to prevent Cu induced damage to DNA.

TABLE 1

| Experiment | Off Powder | Experiment | On Powder |
|---|---|---|---|
| 1 | −0.219 | 7 | −0.566 |
| 2 | −0.499 | 8 | −0.401 |
| 3 | −0.02 | 9 | −0.224 |
| 4 | +0.127 | 10 | −0.525 |
| 5 | −0.206 | 11 | −0.710 |
| 6 | +0.166 | 12 | −0.662 |
| Average | −0.109 | Average | −0.516 |
| Standard Deviation | 0.25 | Standard Deviation | 0.18 |

TABLE 2

|  | Average Slope | % Inhibition | Std |
|---|---|---|---|
| No Cu, no energy (control) | −0.813 |  | 0.06 |
| 1.0 mM Cu, no energy | −0.023 | 97 | 0.015 |
| 1.0 mM Cu with Aulterra's energy | −0.011 | 98 | — |
| 05.mM Cu, no energy | −0.11 | 86 | 0.25 |
| 0.5 mM Cu with Aulterra's energy | −0.52 | 36 | 0.18 |

The Effect of Aulterra's Homeopathic Preparation on DNA

Control water used to make the homeopathic preparation showed similar behavior to that previously observed with deionized water. Preliminary experiments indicated that, depending on the experiment, several different types of responses were observed in DNA exposed to the homeopathic preparation. Sometimes the recovery would initially appear normal (e.g., a steady decrease) but after approximately twenty (20) minutes the DNA would stop rewinding and begin to slowly unwind (positive slope). In other cases it would stop rewinding and remain stationary, i.e., the DNA didn't continue to wind or unwind (e.g., flat slope). In other cases oscillatory behavior was observed very similar to that observed when the DNA was placed on the powder. This oscillatory behavior may be a characteristic response of DNA to Aulterra's energy, whether it be radiating from a powder or "read" by the DNA from information in imprinted water. The non-reproducibility of the phenomenon in regards to the homeopathic preparation is likely due to resonant conditions that have not yet been found experimentally. It is predicted that under the correct resonance conditions, the oscillatory behavior will be more reproducible.

The Ability of Aulterra's Neutralizer to Reverse Harmful Effects of Electromagnetic Fields Generated from Cell Phones on Human DNA Electromagnetic (EM) fields from cell phones were shown to have a statistically significant detrimental effect on the recovery of human DNA after heat shock. Work by Glen Rein, Ph. D. indicated that this effect was observed with cell phones on standby mode when they are emitting relatively weak EM fields and after only minutes of EM field exposure. The detrimental effect of EM energy from cell phones was counteracted, and in this instance completely neutralized, when Aulterra's Neutralizer (e.g., paramagnetic material) was attached to the back of the cell phone. In the presence of the Neutralizer, there was 100% recovery of the DNA as if no cell phone was present. This neutralizing effect appears to prevent initial damage to DNA immediately following EM field exposure.

In the experimental approach, a biological system is influenced by EM fields from cell phones, which in this instance is purified human DNA suspended in a natural ionic environment. Previous studies demonstrated that the secondary structure of DNA is sensitive to classical and non-classical EM fields, thereby indicating that energy fields can influence the winding and unwinding of the two strands which make up the DNA helix and define its conformation.

Because heat shock causes DNA strands to unwind, a sensitive assay was developed which involves measuring the kinetics of rewinding following heat shock. As DNA cools, it gradually rewinds back into an intact double helix. The rewinding process can be monitored by measuring the absorption of UV light as a function of the cooling temperature or increasing time. As the DNA rewinds, hydrogen bonds reform to connect the two strands. Thus the rate of DNA rewinding is directly related to the number of hydrogen bonds formed.

Sodium chloride was added to the deionized water in these experiments to simulate the natural ionic environment of DNA as it normally exists in the human body. Iron was also added since a previous study demonstrated that the sensitivity of DNA to UV light is enhanced in the presence of small amounts of iron (ferric ions). Three types of experiments were conducted in this study. The control experiments were done first in the presence of ambient EM fields, but in the absence of man-made EM fields. In the electromagnetic experiments, DNA recovery was measured in the presence of EM fields from cell phones. The third set of experiments involved measuring DNA recovery in the presence of neutralized EM fields from cell phones containing the Neutralizer.

For the experimental methods, the specific protocol that was followed involved making a stock solution (0.4 mg/ml) of human placental DNA (Sigma Chemical Co., St. Louis) in deionized water. The stock solution was diluted to 0.03 mg/ml in 5 mM NaCl containing 1-4 µM FeCl. A concentration of 1 µM FeCl was shown to be optimal and used in the final experiments. Immediately after heat treatment (80° C. for four minutes) the DNA was transferred to a quartz cuvette and placed in a cuvette holder inside a spectrophotometer. For EM field exposure, a mobile cell phone (popular in the late 1990's) was plugged in, set on standby mode and placed face up on top of the cuvette. The cell phone cord was fed through a hole in the side of the spectrophotometer so the lid could be closed during measurement of DNA rewinding.

To neutralize the EM fields, the Aulterra Neutralizer was placed on the back of the cell phone directly below the antenna. The cell phone containing the Neutralizer was then placed face up on top of the cuvette. In these experiments, normal and neutralized cell phones were identically placed on the cuvette immediately after heat treatment and remained there for the duration of the experiment. The same protocol was used for these two sets of experiments, as well as for controls, which were done in the absence of any cell phone. Controls were done first, followed by the cell phone treatment. Then two weeks time elapsed before beginning the neutralized cell phone experiments to dissipate the cell phone energy and avoid conditioning effects.

For each experiment, the conformation of DNA was measured with state of the art biochemical methodology using a UV-visible diode array spectrophotometer (Hewlett Packard 8451A) to quantify the amount of UV light absorbed. Spectrophotometric measurements were taken every ten seconds for fifteen minutes and began immediately after the cell phones were placed on the cuvette and the lid closed. As the DNA rewinds, the absorption of light gradually decreases. The initial slope of rewinding was calculated using spreadsheet software.

Figure 4:
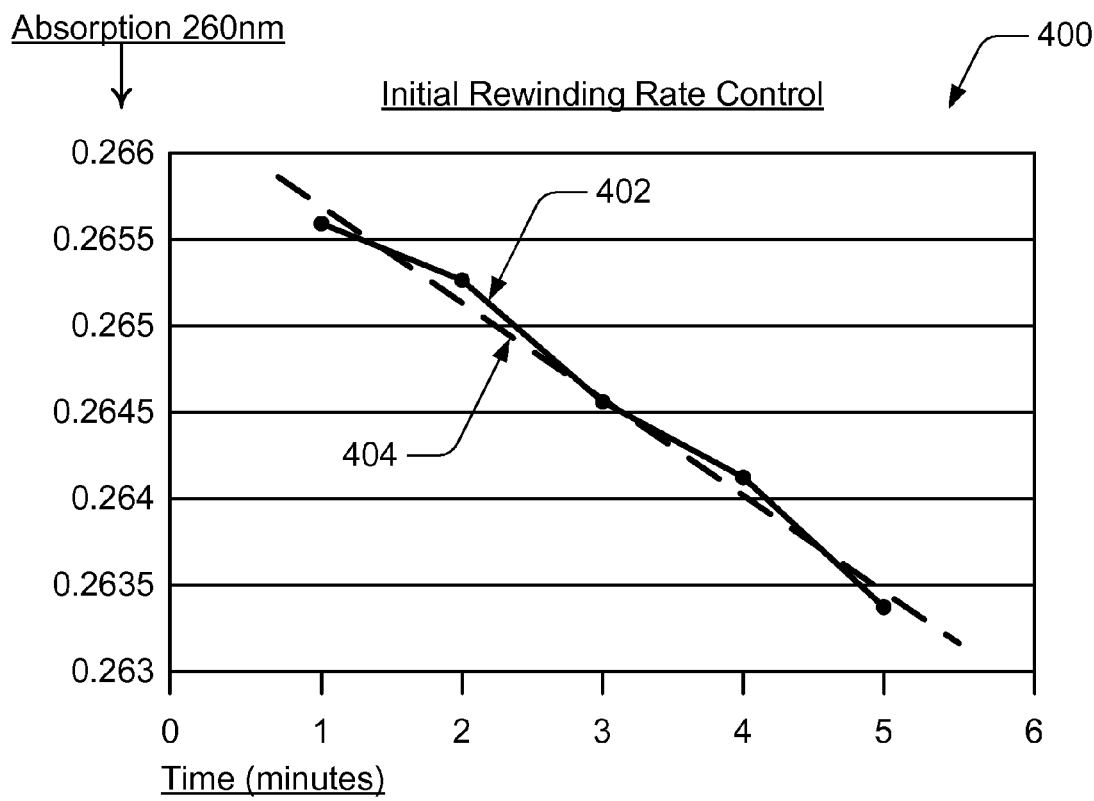
FIG. 4 illustrates an example of an initial DNA rewinding curve.

FIG. 4 illustrates a typical initial rewinding curve 400. The line 402 is a plot of the raw absorption data collected by the spectrophotometer as a function of time after heat shock. The line 404 is the computer generated best-fit calculation of the slope. The slope in this region corresponds to the initial recovery rate, classically used by biochemists in studying enzyme kinetics. The initial slope was calculated for each separate experiment and then compared statistically using a two sample t-test (assuming equal variance). For statistical analyses, a total of six control experiments, eight EM experiments, and six neutralized EM experiments were used.

Electromagnetic Fields from Cell Phones Effect DNA Recovery

The results in Table 3 demonstrate the effect of EM fields from cell phones on DNA rewinding after heat shock. In the absence of EM fields (control experiments), a negative slope for DNA rewinding is obtained. A less negative value for the slope reflects a slower rewinding rate. Therefore, in the absence of EM fields the average slope was −0.877±0.041. In the presence of EM fields from the cell phone the slope had an average value of −0.687±0.189. This indicates that the EM field from the cell phone produced a 22% slow down in DNA rewinding. This detrimental effect of EM fields from the cell phone is highly significant compared to the untreated control ($p<0.02$).

TABLE 3

|  | Avg. Slope | SD | n | p (vrs. control) |
| --- | --- | --- | --- | --- |
| Control | −0.877 | 0.041 | 6 |  |
| Cell Phone | −0.687 | 0.189 | 8 | 0.02 |
| Cell Phone + Neutralizer | −0.872 | 0.063 | 6 | not significant |

Cell Phone Damage Reversed with the Aulterra Neutralizer

The cell phone containing the Neutralizer produced a similar effect on DNA rewinding as was observed in the controls. The average slope for these experiments was −0.872±0.063. This result is not significantly different than the control value indicating that the harmful effect of the EM field from the cell phone is completely neutralized by the presence of the Neutralizer.

A previous study from the Quantum Biology Research Lab (Rein, 2000) demonstrated an unusual effect when a test tube containing human DNA in an aqueous solution was physically placed on top of the Aulterra Powder (e.g., paramagnetic material), the active ingredient of the Neutralizer. The results demonstrated that the powder radiates an energy field which resonates with DNA producing an oscillatory winding and unwinding behavior in its secondary structure. Such behavior is consistent with the newly discovered phenomenon in biological systems referred to as macroscopic quantum coherence and suggests that the energy radiating from the Aulterra Powder is highly coherent (e.g., laser-like). Since the paramagnetic material in the powder will radiate classic (incoherent) EM energy, it is conceivable that the activation procedure in the manufacturing of the powder makes this intrinsic energy coherent. Alternatively, the unique mixture of minerals in the Aulterra Powder may have intrinsic quantum properties, like other complex lattice structures which also exhibit quantum properties.

The ability of Aulterra's Powder to radiate quantum fields is related to its ability to store quantum information following activation. Quantum information storage is now a recognized technology in the computer industry which involves optical and magneto-optical storage. Information storage in computers and in Aulterra's products share a common mechanism, since they both use an external EM field to store information and both result in the emission of a different type of EM field. Some variations of computer technology allow storage of information in three dimensional lattice structures, similar to Aulterra's mineral base. In other variations of computer technology, the emitted EM field can be a coherent laser. Furthermore, certain storage media exhibit unusual anomalous behavior referred to as space-inversion symmetry (i.e., normal symmetry associated with magnetization of the optical materials is broken). A similar situation also exists in phase conjugating systems where a time-reversed longitudinal wave is emitted. According to quantum physics, both of these situations occur at the quantum level and are associated with the presence of quantum fields. Therefore, if these established systems are capable of emitting a quantum field, Aulterra's technology may also do the same.

If the Aulterra Powder radiates a highly coherent field, how could such a field neutralize the harmful, incoherent radiation emitted from a cell phone? Although traditional physics theory states that two force fields don't interact in space (e.g., they pass through each other), recent experiments indicate that such interactions are possible. Working with two incoherent light sources, a demonstration was made that one could modulate the action of the other to modulate a chemical reaction. In addition, another demonstration was made that energy associated with a chemical enzyme inhibitor, in powder form, could produce a biological effect when the molecular energy was used to modulate a laser. In this sense, the coherent laser energy acted as a carrier for the molecular energy. These studies demonstrate that two energy fields can in fact interact. Furthermore, mixing incoherent and coherent energies can have differential effects on biological systems, since a critical ratio of incoherent to coherent energy is required to observe biological effects.

These studies offer an explanation for the ability of a coherent field generated from the Aulterra Powder to neutralize the biological effects of incoherent energy from a cell phone. These studies also explain the results in the previous study by the Quantum Biology Research Lab. Coherent energy from the Aulterra Powder could therefore neutralize the detrimental biological effect of the chemical energy associated with heavy metals. In these experiments, however, the biological system (DNA) was being influenced by both the energy from the chemical toxin and the chemical toxin itself. Nonetheless, the Aulterra Neutralizer offered complete protection.

The Aulterra Neutralizer Reduced the Intensity of Cell Phone Radiation

There is now accumulating scientific evidence that cell phone radiation is harmful to the body. Some have suggested that these reports have been countered with studies that are biased in their experimental design to favor conditions expected to show little to no effects. For example, most of these studies use single isolated frequencies known to be emitted from cell phones. However, studying the biological effects of isolated cell phone frequencies is a reductionist approach. From a biological point of view, the sensitivity of an organism to an individual cell phone frequency is different than the broader complete spectrum of frequencies actually emitted by cell phones. In addition, experiments are often done using low radiation doses, referred to as specific absorption rates (SAR). Thus, experiments designed to show biological damage use doses as high as 100 W/kg. Experiments designed to show no damage use doses as low as 0.08 W/kg, a 1200 fold lower dose.

The fact that higher doses produce stronger damaging effects is the scientific rationale for using headsets which reduce the intensity of the radiation by physically placing the cell phone away from the brain. Unfortunately, this approach just shifts the problem to another part of the body, since these cell phone users typically wear their phones on the belts, thereby exposing reproductive organs to harmful radiation. It was therefore of interest to determine whether the Aulterra Neutralizer (e.g., paramagnetic material) might reduce the intensity of cell phone radiation.

The intensity of cell phone radiation is typically measured using a special type of magnetometer. Magnetometers measure the overall intensity of cell phone radiation across many frequencies comprising the electromagnetic spectrum. In the experiments presented here, radiation emitted by a cell phone and a wireless 2.45 GHz phone was measured by placing a cell phone antenna, tuned to the specific frequencies emitted by these devices, next to the unit while receiving an active transmission. The signal detected by the antenna was then transferred to a spectrum analyzer.

A spectrum analyzer is a sophisticated magnetometer which can measure the intensity of the cell phone radiation at each frequency across the entire broad spectrum emitted by the cell phone. It can also measure the intensity of the radiation at a specific frequency. Six separate analyzer graphs of the intensity of the emitted radiation versus frequency were recorded under each of the experimental conditions defined below. Representative graphs of the background and the signal with and without the Neutralizer are presented here for each of the experimental conditions. To allow direct comparison of graphs with and without the Neutralizer, these graphs have the same intensity scale (y-axis). In some experiments, particularly those with interfering signals from nearby cell phones, the starting reference baseline values were different. In the third experiment, human voice patterns were generated by calling the local weather station which broadcast a recording of the human voice. The experimental conditions for each of the four experiments reported here are summarized below.

Results and Discussion, Experiment #1

Figure 5:
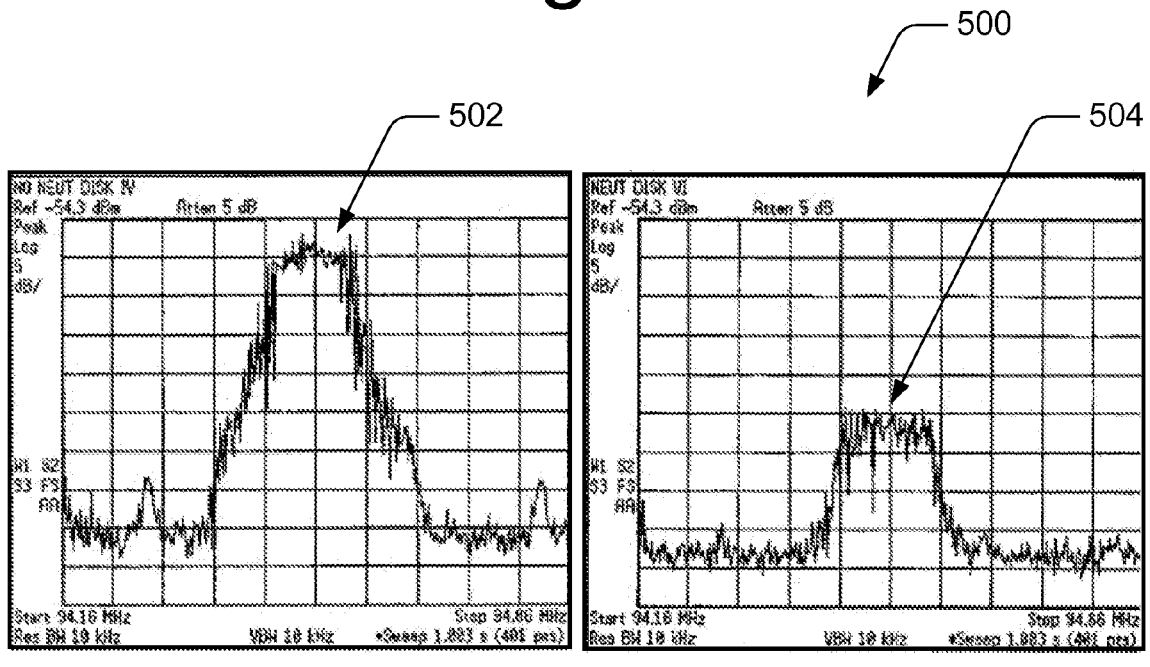
FIG. 5 illustrates a spectrum of measured frequencies radiating from a cell phone to illustrate an embodiment of electromagnetic radiation transformation utilizing paramagnetic material.

FIG. 5 illustrates that a broad spectrum of frequencies 500 radiating from the cell phone could be measured which were significantly above background fluctuations. Large discrete peaks occurred at specific frequencies, e.g., 54, 72, and 94 MHz. For example, a large peak 502 is measured from the cell phone operating without the addition of paramagnetic material. In addition, smaller peaks occurred on either side of these main peaks, assumedly due to the information being transmitted over the open line. When the Neutralizer (e.g., paramagnetic material) was placed in the phone, the side peaks disappeared and the main peak 504 was reduced in size by half. This reduction in intensity was observed qualitatively at each of the main peaks but was also studied quantitatively in detail using the 94 MHz peak. The experiment was done six times with and without the Aulterra Neutralizer in the cell phone. The average intensity of the 94 MHz peak was 36.4±1.3 dBm. With the Aulterra Neutralizer, this peak decreased in size to a value of 17.6+2.5 dBm. This 52% (2-fold) reduction is highly statistically significant ($p<0.0001$).

Results and Discussion, Experiment #2

Figure 6:
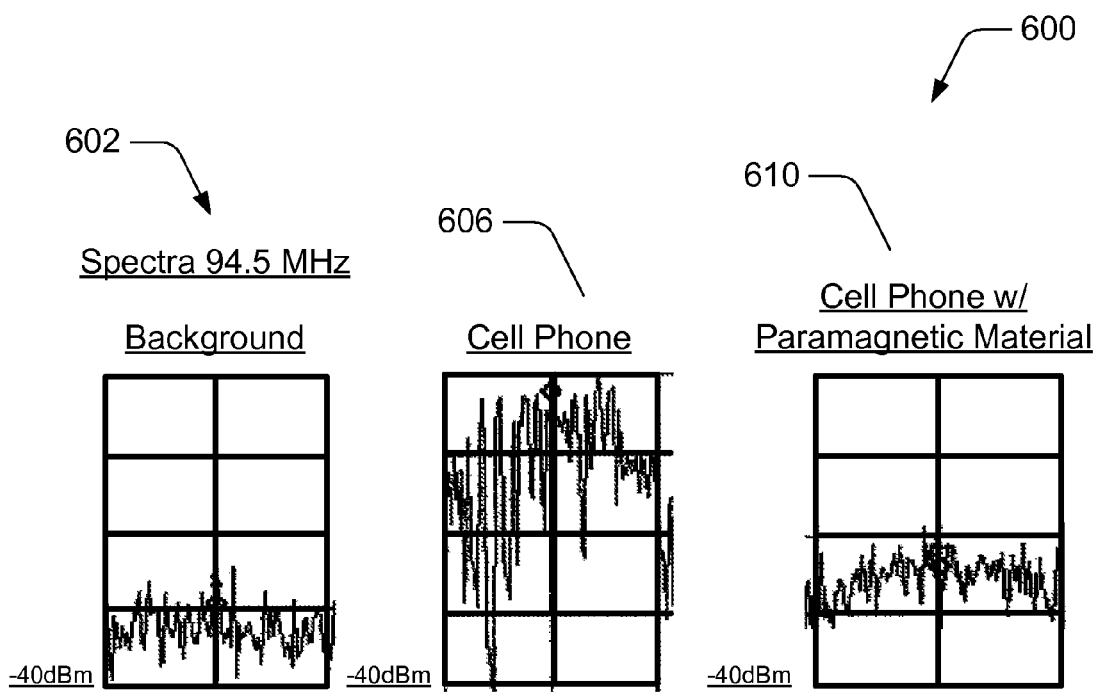
FIG. 6 illustrates detected cell phone signals over background noise to illustrate an embodiment of electromagnetic radiation transformation utilizing paramagnetic material.
Figure 6:
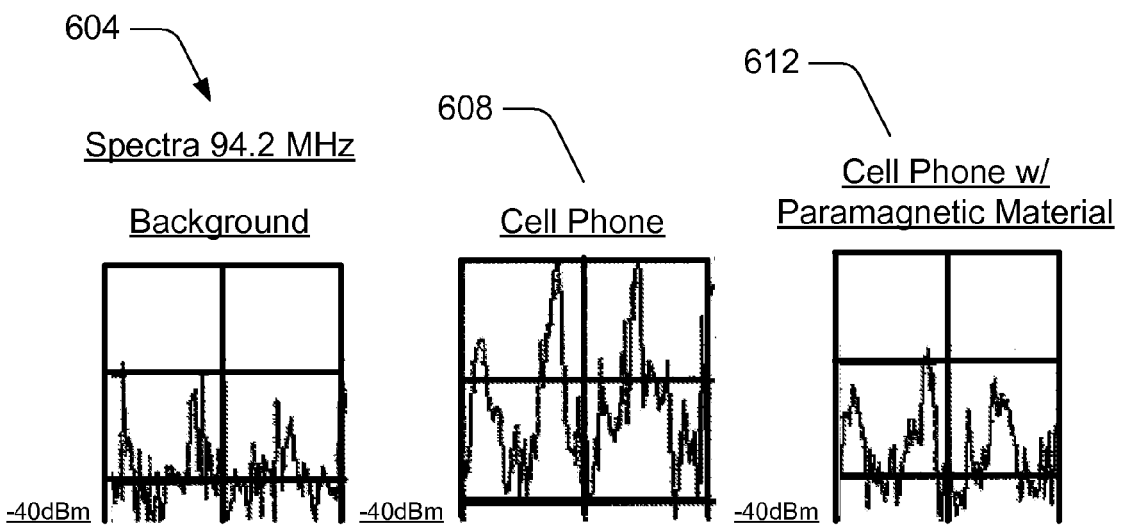

FIG. 6 illustrates experiments 600 in which the background was not flat and weak as in previous experiments, but contained several flattened peaks in the same region as previously observed, indicating the presence of a nearby interfering cell phone in the immediate environment. Despite the presence of this strong environmental noise (e.g., "background"), the cell phone signal could still be detected above the background signal. The efficacy of the Aulterra Neutralizer to reduce the cell phone radiation is shown in two different frequency regions 602, 604 where the cell phone signal was at least twice that of the background signal.

Since in this experiment each box is 7 dBm high, the average background value was 45 dBm. The cell phone signal 606, 608 showed strong peaks reaching a maximum value of 66 dBm. In the presence of the Neutralizer (e.g., paramagnetic material), the same cell phone produced signals with an intensity corresponding to 50 dBm. Subtracting the background contribution to the signal, the cell phone signal was 21 dBm and the neutralized (e.g., altered or transformed) cell phone signal 610, 612 was 5 dBm. This corresponds to a 76% (4-fold) reduction of the signal in the presence of the Neutralizer.

In this portion of the EM spectrum, it is clearly visible that the cell phone signal 610, 612 in the presence of the Aulterra Neutralizer is quantitatively and qualitatively similar to that obtained from the background. It is interesting to note that although the three peaks attributable to the cell phone are significantly reduced in the presence of the Neutralizer, they can still be made out.

Results and Discussion, Experiment #3

Figure 7:
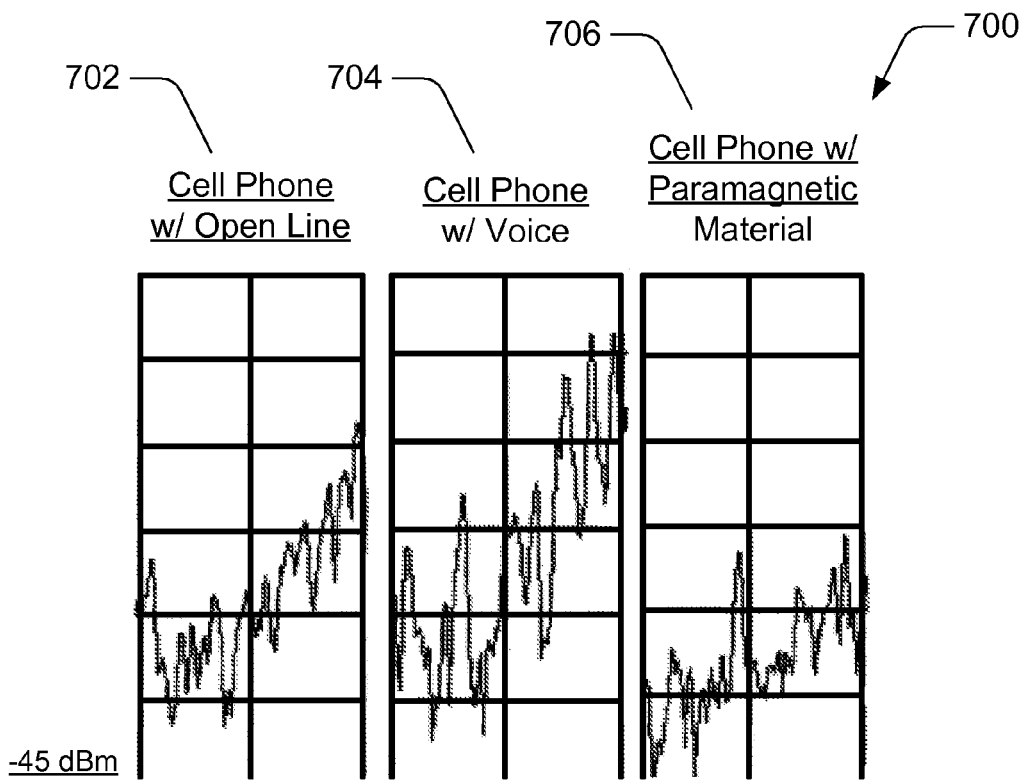
FIG. 7 illustrates detected cell phone signals to illustrate an embodiment of electromagnetic radiation transformation utilizing paramagnetic material.

FIG. 7 illustrates an experiment 700 that was designed to compare the cell phone signal 702 with an open line and the signal 704 when the human voice was being transmitted over the line. A high background was observed indicating the presence of an interfering cell phone. The measured signal 704 from a cell phone with voice patterns was significantly larger and more irregular (chaotic) than the signal 702 with an open line. The voice signature is most apparent on the shoulder of the main cell phone peaks. In the presence of the Neutralizer (e.g., paramagnetic material), the voice signature 706 was significantly reduced in amplitude.

Results and Discussion, Experiment #4

Figure 8:
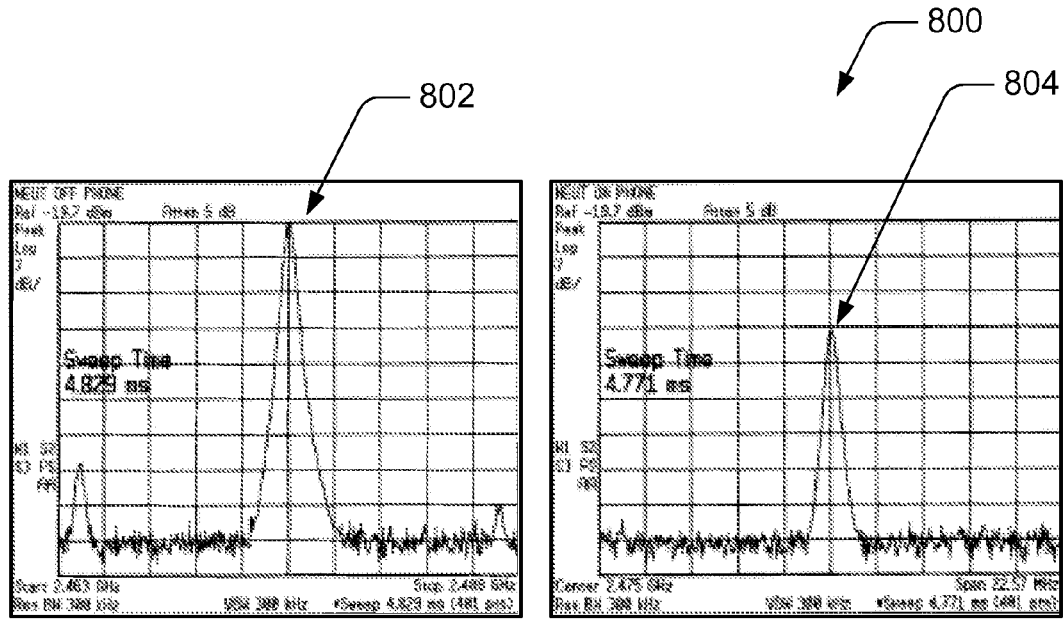
FIG. 8 illustrates measured frequencies radiating from a cell phone to illustrate an embodiment of electromagnetic radiation transformation utilizing paramagnetic material.

FIG. 8 illustrates experiments 800 in which the background noise was weak. The wireless phone (e.g., a cordless basestation phone) generated a peak 802 at 2.48 GHz with two smaller side peaks on either side of the main peak. This experiment was analyzed quantitatively using individual values from the six separate experiments. In the absence of the Aulterra Neutralizer (e.g., paramagnetic material) the amplitude of this main peak 802 was 61.0±1.64 dBm. With the Aulterra Neutralizer the intensity was reduced to 42.9±1.16 dBm at 804. This 30% reduction was statistically significant ($p<0.0001$). Thus, the Neutralizer is somewhat less effective at reducing this peak than the peaks obtained from a cell phone. This is expected since the total radiation emitted from a cell phone is distributed amongst several frequency bands which are less intense than the strong peak obtained for the wireless phone. As previously reported for the cell phone, both side peaks associated with information being transmitted were completely eliminated by the Neutralizer.

The results of these experiments indicate that the Aulterra Neutralizer weakens cell phone and wireless phone radiation by reducing the intensity of their signature frequency peaks. In all experiments, the Aulterra Neutralizer was effective across the entire radio and microwave spectrum of radiation emitted by these devices. This inhibitory effect was also independent of the various experimental conditions, i.e., whether there were interfering cell phone signals in the immediate environment or whether there were human voices being transmitted over the line. In some experimental conditions the neutralized phone had radiation emissions similar to those of the background ambient noise.

This new data should be taken in conjunction with the previous observation that the Neutralizer also reduces the damaging effects of cell phone radiation as measured by changes in the conformation of human DNA. This latter result indicates that the Neutralizer is protecting a key biological system from the detrimental effect of cell phone radiation. The results from the present study suggest that the bio-protective effect of the Neutralizer is in part due to the reduction in the intensity of the offending radiation. The results of both studies taken together indicate that the Neutralizer protects the body by two different mechanisms, a biochemical defense response and a physical alteration of the cell phone signal.

Mitigating the Biological Effects and Radiation Intensity of Cell Phones

Maria Syldona, Ph.D. has stated in an article that several studies have demonstrated detrimental effects of cell phone radiation on biological systems when resonance conditions are met and therefore submits the following article. This article introduces a novel in-vitro method for demonstrating conformational changes in human DNA induced by a five minute exposure to cell phone radiation emitted by an actual contemporary cell phone. Dynamic changes in DNA conformation were assessed in real-time by measuring the rate of renaturation following heat shock. Cell phone radiation produced a 40% increase in the rate of DNA renaturation. This effect was completely attenuated when the experiment was repeated with the same cell phone containing a commercially available shielding technology. In a separate series of experiments the intensity of the cell phone radiation was measured using a Spectrum Analyzer. The intensity was reduced by approximately 50% in the presence of the shielding technology. Taken together, these studies indicate a new method of mitigating the biological effects of cell phone radiation.

While there is growing evidence that many types of electromagnetic (EM) energies such as those involved in bone healing, wound healing and pain relief have beneficial effects on the body, other types of EM field are harmful. For example, x-rays and ultraviolet light have been long known to damage the body. Other portions of the EM spectrum are currently being studied by the Bioelectromagnetics community of scientists who study electro-pollution and make recommendations to the government regarding public safety. Radio frequency and microwaves, as well as power line frequencies which are emitted by modern household and communications devices, have been asserted to have detrimental effects on the body. These effects, however, can be somewhat elusive since specific experimental conditions are required for a resonance interaction between EM fields and their biological targets. These conditions are not always met in certain experimental designs.

More recently cell phones have become of interest. Several clinical studies have been published in peer-reviewed journals demonstrating detrimental effects of cell phone radiation. Carcinogenic effects of cell phone radiation are of particular concern since several peer-reviewed studies have demonstrated genetic damage. Epidemiological studies have demonstrated a statistically significant association between radio-frequency cell phone radiation and cancer with an increase in disease incidence with increasing exposure. Increased tumor incidence in animal studies as well as in-vitro studies corroborates the clinical studies. Direct effects on DNA offer a feasible mechanism of action as studies have demonstrated cell phone radiation induces strand breaks.

The present study measured the effects of cell phone radiation on DNA conformation in-vitro and measured the intensity of the radiation emitted by cell phones. DNA conformation was measured using classical renaturation techniques. The intensity of cell phone radiation was measured using a spectrum analyzer. The results demonstrate that cell phone radiation speeds up DNA renaturation and that this effect is prevented when a commercially available processed mineral is placed in the presence of the cell phone radiation. A second series of experiments demonstrated that this same shielding device also reduced the intensity of radiation emitted from cell phones.

In the first series of experiments, conformational changes in human DNA were measured in this study by monitoring renaturation in real-time. The procedure involved measuring the recovery of DNA after heat shock known to denature the two strands of the double-helix. After heating, the DNA quickly recovered by rewinding back to its original intact conformation. The rewinding process can be monitored by measuring the absorption of light by chromophores in the DNA strands. Control experiments were conducted first in the presence of ambient EM fields. Then DNA rewinding was measured in the presence of the cell phone. In the third experimental condition, DNA rewinding was measured using the same cell phone containing an Aulterra Neutralizer (e.g., paramagnetic material) placed on the battery inside the cell phone. A second series of experiments was conducted to determine the efficacy of the Aulterra Neutralizer in reducing the radiation emitted by a cell phone. The intensity of the emitted radiation was measured using a spectrum analyzer.

DNA Rewinding Assay (Series I)

To determine the effect of cell phone radiation on a model biological system, DNA renaturation was measured. A stock solution of human placental DNA (Sigma Chemical Co., St. Louis) in deionized water was further diluted to 0.03 mg/ml in deionized water and heat shocked for four (4) minutes at 80° C. Immediately after heat treatment the DNA was transferred to a quartz cuvette and immediately measured in a spectrophotometer with the lid closed. For EM field exposure, a cell phone (2004 model), in receiving-mode with no human voice transmitted, was placed face down on top of the cuvette inside the spectrophotometer. The cell phone remained in this position for the duration of the five minute experiment. The exact procedure was then repeated using the same cell phone containing the Aulterra Neutralizer.

Absorption of light at 260 nm was measured using a UV-visible diode array spectrophotometer (Hewlett Packard 8451A) every ten seconds over a five minute time period. As the DNA rewinds, its ability to absorb light decreases with time. The initial slope of the rewinding curve, typically used when studying kinetics of biochemical reactions, was calculated using spreadsheet software. All rewinding curves had a negative slope value. Slope values for the different experimental conditions were analyzed for statistical significance using a two sample t-test (assuming equal variance). A total of twelve (12) control experiments, fourteen (14) cell phone experiments and twenty-two (22) neutralized cell phone experiments were used for these analyses.

Measurement of Cell Phone Radiation (Series II)

This series of experiments was designed to test the ability of the Aulterra Neutralizer to reduce the intensity of radiation emitted by a cell phone. The radiation emitted by the same cell phone used in Series I was measured by placing a cell phone antennae on top of a cell phone while receiving an active transmission. Such antennae are tuned to the specific frequencies emitted by cell phones. For some experiments the phone was receiving a repeating, pre-recorded weather channel transmission. The signal detected by the antenna was then transferred to a spectrum analyzer (Agilent ESA-E series with FM modulation). Six separate analyzer graphs, plotting intensity of emitted radiation vs. frequency, were generated from the cell phone and six additional graphs were generated using the same phone containing an Aulterra Neutralizer. Representative graphs are presented here for each of the experimental conditions. To allow direct comparison of graphs with and without the Neutralizer, these graphs have the same Db intensity scale (y-axis).

Figure 9:
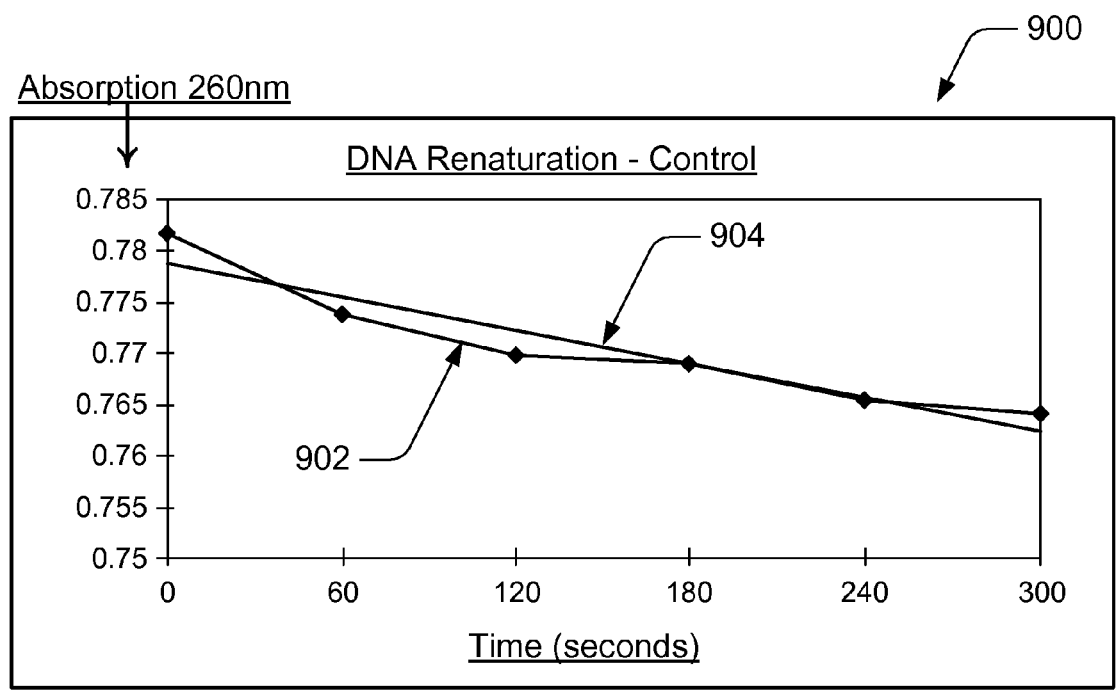
FIG. 9 illustrates an example of an initial DNA renaturation curve.

FIG. 9 shows a typical initial DNA renaturation curve 900 over several minutes. The irregular line 902 is a plot of the raw absorption data collected by the spectrophotometer. The line 904 is the computer generated best-fit calculation of the slope.

Electromagnetic Fields from Cell Phones Effect DNA Renaturation

The results presented in Table 4 below indicate the effect of cell phone radiation on DNA renaturation after heat shock. In the absence of cell phone radiation (control experiments), the average slope over all twelve experiments was −0.41±0.065. In the presence of EM fields from the cell phone, the slope had an average value of −0.56±0.056 over all fourteen experiments. A more negative value for the slope reflects a faster rewinding rate following heat shock. Therefore, the EM field from the cell phone produced a 40% increase (relative to control values) in the rewinding rate. The magnitude of the effect varied from 20-58% depending on the experiment. This effect of the cell phone radiation is highly statistically significant compared to the untreated control ($p<0.0001$).

TABLE 4

| | Avg. Slope | SD | % change | n | p (wrt control) |
|---|---|---|---|---|---|
| Control | −0.41 | 0.065 | | 12 | |
| Cell Phone | −0.559 | 0.056 | +40 | 14 | <0.0001 |
| Cell Phone + Neutralizer | −0.43 | 0.115 | +5 | 22 | not significant |

Aulterra Neutralizer Attenuates Cell Phone Induced Effects on DNA

Figure 10:
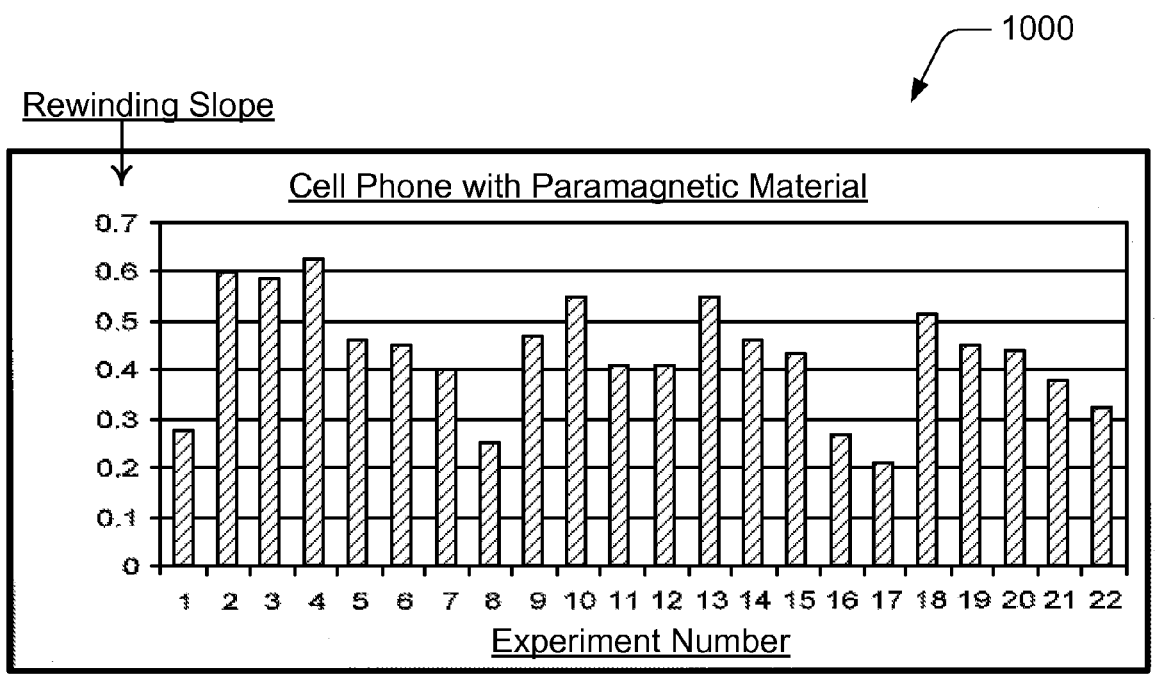
FIG. 10 illustrates the effect of a cell phone containing shielding technology (e.g., paramagnetic material) on DNA renaturation.

The results in Table 4 indicate that the cell phone containing the Neutralizer produced an average slope of −0.43±0.11 for all 22 experiments. This average value is not significantly different than the control value indicating that the effect of the cell phone radiation on renaturation is completely reversed in the presence of the Neutralizer. When examining the data 1000 from the individual experiments as shown in FIG. 10, however, it is apparent that on some occasions the cell phone radiation is not neutralized (e.g., experiment numbers 2, 3, 4, 10, and 13). This indicates that for these particular treatment sessions, on a given day, resonance conditions were not met. FIG. 10 illustrates the effect of a cell phone containing paramagnetic material on DNA renaturation, and includes the average slope values for each of twenty-two (22) experiments.

Aulterra Neutralizer Reduces Cell Phone Radiation

Several discrete frequencies emitted from the cell phone could be measured with the spectrum analyzer, which were significantly above background fluctuations. Large discrete peaks occurred at specific frequencies, e.g., 54, 72, and 94 MHz. In the presence of the Aulterra Neutralizer (e.g., "With Paramagnetic Material" as shown in FIG. 5) a reduction in the intensity of all peaks was observed and the peak at 94 MHz was studied quantitatively. Over six experiments, the average intensity of the 94 MHz peak was 36.4±1.3 dBm. With the Neutralizer this peak decreased in size to a value of 17.6±2.5 dBm. This 52% (2-fold) reduction is highly statistically significant ($p<0.0001$). Since the two smaller side peaks were absent when measuring a signal from an open channel with no human voice transmission, they are likely due to human voice modulation of the cell phone signal. In the presence of the Neutralizer, both side peaks were completely eliminated.

Experiments performed in Series I utilize a classical property of DNA, renaturation, as a new model system for studying in-vitro effects of cell phone radiation. The results indicate that cell phone radiation significantly speeds up the rate of rewinding. This effect is highly reproducible in the fourteen (14) independent experiments with a magnitude that varied between 20% and 58%. The effects observed on DNA conformational states in the present study suggest a particular resonance between cell phone radiation and hydrogen bonds which hold together the two strands of the DNA helix. Other similar types of EM fields have also been shown to effect DNA conformation. Hydrogen bonds also maintain the secondary structure of other important bio-molecules like chromatin, whose conformation is also sensitive to the cell phone radiation. If cell phone radiation is shown to have a direct effect on hydrogen bonds in general, the implications for biology could be profound. This hypothesis is feasible because hydrogen bonds have vibrational modes in the microwave region where cell phones emit.

The ability of cell phone radiation to effect DNA conformation is supported by a hypothesis stating that DNA itself can act as a target for EM fields. Additional support comes from studies demonstrating that cell phone radiation can directly break (nick) one or both DNA strands, whereas other types of EM fields alter DNA synthesis. Although conformational changes cannot be considered harmful, per se, other EM field effects on DNA are clearly detrimental.

Typically, harmful effects have been studied using individual frequencies known to be generated from cell phones and only few studies use actual cell phones which emit a complex mixture of individual frequencies. DNA nicking (e.g., induced by cell phones) is known to be associated with subsequent development of cancer. Since the implications for public health are profound, methods to mitigate the harmful effects of cell phone radiation are currently being sought. New technologies have emerged utilizing a novel concept that one type of EM field can reverse or neutralize the biological effects produced by another type of EM field. This has been demonstrated through an observation that a second orthogonal light beam could interact with and neutralize the biological effects induced by a first light beam. Similar results were demonstrated with DC magnetic fields capable of neutralizing the effect of a pulsed magnetic field on neurite outgrowth in neuronal cells. Yet another similar phenomenon was demonstrated using incoherent noise fields to neutralize magnetic field effects on ornithine decarboxylase induction. At least one example of how this technology can be applied to cell phone protection was recently demonstrated in a study using a commercially available shield. In this study the number of fruit fly offspring was used as a model system and shown to be sensitive to cell phone radiation. This effect was reversed when a commercially available aluminum shield was added to the cell phone The present study demonstrates a similar phenomenon, but utilizes a different model system. Here the cell phone induced changes in DNA renaturation are completely reversed when an Aulterra Neutralizer (e.g., paramagnetic material) is added to the cell phone. This effect is seen 77% of the time yielding an overall statistically significant effect. The fact that this effect is not seen in every experiment is interesting and suggests that resonance conditions are not met in every experiment. So far resonance conditions have been characterized in terms of narrow frequency and amplitude windows.

In the present case, resonant conditions involve a complex interaction between two EM fields and the DNA molecule. The second EM field, admittedly weak, is expected to be generated from the Aulterra Neutralizer itself. In other similar systems (described above), where two EM fields interact, the strength of and orientation between the two fields is critical in order to obtain resonance conditions.

In the present experiment, off-resonance conditions occur only 23% of the time. Experiments can be designed in such a way that off-resonance conditions occur frequently enough to conclude cell phone radiation produces no damaging effects.

Many of the scientific studies reported in the literature utilize such experimental designs. Redesigning such experiments can produce on-resonance conditions so that cell phone effects can be measured. In real-world situations consumers are chronically exposed to cell phone radiation which at times is either on or off-resonance.

Preliminary experiments indicate that the Aulterra Neutralizer contains a highly paramagnetic mineral. It is therefore conceivable that a magneto resistance response (Meissner effect) is induced when the Neutralizer is in the presence of the magnetic fields generated from cell phones. Thus paramagnetic shielding (in addition to ferromagnetic shielding) is a likely explanation for the ability of the Neutralizer to reverse the effects of cell phone radiation on DNA renaturation observed in this study. Ferromagnetic transduction has been previously proposed to mediate biological effects of cell phones because of their resonance with the biological mineral magnetite. Furthermore, the fact that the Meissner effect is dependent on magnetic field orientation can also explain off-resonance conditions and why these and other similar experiments are not 100% reproducible.

The reversal of DNA renaturation effects observed in Series I of the present study is further supported by the results obtained by measuring cell phone radiation using a spectrum analyzer (Series II). Specific absorption rates are typically used to quantify the intensity of cell phone radiation, which in turn is related to the severity of the biological damage and therefore public safety. The results of the present study clearly indicate that the intensity of the radiation emitted from cell phones is reduced by approximately 50% in the presence of the Aulterra Neutralizer. In all experiments, the Neutralizer was effective across the entire radio and microwave spectrum of radiation emitted by these devices. This neutralizing effect was also independent of the various experimental conditions, i.e., the presence of voice patterns or EM signals from nearby electronic devices.

When the spectrum analyzer data is taken in conjunction with the DNA data, a strong case may be made for concluding that the Aulterra Neutralizer is capable of protecting the body from cell phone radiation. Although the bio-protective effect may be a result of reducing the intensity of the cell phone radiation, it is also possible that a weak EM field generated by the Neutralizer could have a direct stabilizing effect on the DNA. Therefore, the Aulterra Neutralizer appears to protect the body by both a biological and a physical mechanism. This is the first report of any commercially available cell phone shielding device capable of such a dual action.

Although the cell phone induced changes in DNA conformation measured in this study cannot be considered biologically detrimental, the results support previous studies demonstrating that DNA does in fact directly interact with cell phone radiation. The in-vitro effect produced by such radiation was completely reversed when the cell phone contained a commercially available shielding technology. This finding, when taken together with experiments demonstrating that the shielding device also reduced the intensity of cell phone radiation, supports the conclusion that the Aulterra Neutralizer mitigates the effects of cell phone radiation on DNA in-vitro. It is presently unknown whether this protective effect extends to in-vivo conditions.

Cell Phone Radiation Induced Changes in Human DNA

As previously described, electromagnetic fields (EMF) in the form of x-rays, ultraviolet, microwaves and so on may cause damage to the body. Other portions of the electromagnetic (EM) spectrum, including radio frequency waves emitted from cell phones, computers, television and other devices may also be harmful to the body. Government funded research by the Bioelectromagnetics community has now focused on the health hazards of cell phones due to their endemic use. Of the large number of studies, measured biological effects of actual, broad-spectrum cell phone radiation (not isolated or simulated components) show some detrimental effects.

As previously observed by the Bioelectromagnetic community with video display monitors, biological effects of such radiation are typically observed when resonance conditions are met. It is now well established that many confounding variables, e.g., the strength and orientation of the geomagnetic field, can create experimental conditions where biological effects are not observed. Thus, studies which failed to measure biological effects from cell phone radiation have may not have experienced the resonance conditions which cause the effect to be observed. Therefore, although it is tempting for cell phone manufacturers to focus on studies showing little to no effects and conclude that cell phone radiation is safe due to these observations in non-resonant conditions, real-life cell phone users may be exposed to this radiation numerous times during the course of a day and over the course of several years. Further, most scientific studies do not take into account the chronic use of cell phones.

In some cases, bio-molecular sensors which resonate with the harmful radiation are known. Unfortunately, the most fundamental molecule in the body, DNA itself, can act as a target for such radiation even when it is non-ionizing and at a relatively low-level. A recent study concluded that radiofrequency EMF from cell phones, at intensities similar to those emitted from contemporary cell phones, directly damage DNA. This is the same type of damage previously shown for UV and x-rays. Previous research with other types of EMF, not necessarily emitted by cell phones, indicated shape (conformation) changes in DNA. Either strand breaks or conformational changes in DNA can result in the formation of damaged proteins in the body.

Therefore, there is a continuing need for technology that counteracts (e.g., blocks or neutralizes) cell phone radiation. Since the radiation emitted from cell phones is relatively strong, inert materials which can absorb the radiation to significantly reduce the body's exposure may not be readily available. An alternative approach is to use materials which radiate EMF of their own to neutralize the cell phone radiation. There are several examples in the scientific literature where one type of radiation will neutralize another, which is described in further detail below. The Aulterra Powder is an example of such a material which, because of its paramagnetic properties, radiates an EMF which counteracts (e.g., neutralizes) the damaging effects of cell phone radiation on DNA.

A highly sensitive bioassay has been developed by the QBRL (Quantum Biology Research Laboratory) to quantify EMF effects by measuring conformational changes in human DNA. The procedure involves measuring the rewinding of DNA after heat shock, which unwinds the two strands that make up the DNA double-helix. After heating, the DNA rewinds back to its original intact conformation. The rewinding process can be monitored by measuring the absorption of light as the DNA cools.

The results of this study indicate that cell phone radiation speeds up rewinding of DNA after heat shock. This study replicates the results of a previous study with the Aulterra Neutralizer. However, the previous study used an older cell phone technology no longer in use and was done with a cell phone in "stand-by" mode. The present study used a cell phone popular around 2002 which was tested while in a "receiving" mode.

In the previous study, cell phone radiation slowed down DNA rewinding. These opposite effects could be due to the fact that different types of cell phones (new vs. old technology) were used in the two studies and they were used in different modes (stand-by mode vs. operating mode). A cell phone in operating mode will generate a stronger EMF. Other scientific studies have observed that the direction of a biological effect is dependent on the intensity of the applied EMF with opposite effects at high and low doses.

The sensitivity of DNA to EMF is also dependent on its ionic environment. In the previous study, DNA was surrounded by sodium and iron ions which are known to bind to DNA and influence its helical structure. Iron is ferromagnetic and influences the susceptibility of DNA to EMF. Furthermore, the iron and possibly even the sodium ions themselves could absorb EM radiation and complicate the interpretation of the results, since these ions are known to mediate biological effects of EM fields. The interaction of different ions with DNA and the cell phone radiation is complex and could account for the opposite effects observed in the two studies.

The results of the present study confirm those of the previous study thereby demonstrating that cell phone induced changes in DNA are completely reversed when an Aulterra Neutralizer (e.g., paramagnetic material) is added to the cell phone. In the present study, the cell phone effect on DNA was twice as strong as before (40% vs. 22%) and the Neutralizer still showed 100% protection. In some experiments not only did the elevated slope values return to normal, but they went below control values. This indicates that in approximately one-fifth of the experiments, the neutralized CP radiation actually slowed DNA rewinding. It is therefore predicted that when these resonance conditions are met, the neutralized CP radiation could actually have a beneficial effect on the body.

It was previously observed that the EMF generated from the Aulterra Powder induces an oscillatory winding and unwinding behavior in DNA. Since rewinding of DNA strands involves the formation of hydrogen bonds, which exhibit quantum properties, it was proposed that the Aulterra Powder radiates a quantum field which is highly coherent (e.g., laser-like). This observation was offered as a feasible mechanism to explain how the Aulterra Neutralizer could cancel the detrimental effects of cell phone radiation, since it is known that adding coherent information to a classical EMF modifies its ability to influence biological systems.

Additional scientific literature indicates that other mechanisms are also likely to explain the results of the present study. These studies do not require that the EMF radiating from the Aulterra Powder be coherent, but rather indicate that even classical EMF emissions can produce the same neutralizing effects. Paramagnetic substances like the Aulterra Powder can both generate magnetic fields (due to the presence of unpaired electrons) and can absorb magnetic fields (a property called magnetic susceptibility).

Thus, it is likely that the Aulterra Powder also generates a classical EMF which can couple to and neutralize the EMF from the cell phone. Although classical EMF theory does not predict that two interacting EMF can influence each other, scientific evidence indicates that the biological activity of one EMF can be altered in the presence of a second EMF. For example, an interaction between two perpendicular, high-frequency EMFs in air which annihilated the effect of the primary EMF on the crystalline lattice structure of an enzyme substrate has been observed. More recent experiments combine low frequency EMF with static magnetic fields.

These experiments indicate a complex interaction between the two fields where the biological activity of the low frequency EMF can either be enhanced or reduced depending on the orientation and the amplitude of the two fields. In some orientations and amplitudes, no modulation of the biological activity is observed. Therefore, interaction between the two fields may occur under certain resonance conditions and not others. In the present study there is also a complex interaction between the EMF radiating from the cell phone, the energy radiating from the Neutralizer (e.g., paramagnetic material), and the geomagnetic field. Although reported resonance occurs under certain correct conditions, in the present study, the cell phone radiation was still completely neutralized by the energy radiating from the Neutralizer.

Electromagnetic Radiation Transformation for Powered Devices

Embodiments of electromagnetic radiation transformation for powered devices can include devices, systems, and/or procedures that may utilize paramagnetic and/or diamagnetic techniques to transform electromagnetic frequencies (e.g., radio frequencies), electromagnetic interference or fields, and/or electro-pollution all which may be commonly referred to as electromagnetic radiation, "EMF", or "EMF radiation".

In various embodiments, a wireless phone, such as a cordless phone, cellular phone, or other similar device includes one or more sources that emit electromagnetic radiation, such as an internal power supply or antenna system. The wireless phone can also include paramagnetic material in a quantity sufficient to counteract the electromagnetic radiation emitted by the source(s). To counteract harmful effects of the electromagnetic radiation, the paramagnetic material can transform the electromagnetic radiation, such as to effectuate a frequency transformation and/or to alter an intensity or waveform of the electromagnetic radiation.

In another embodiment, a casing that supports the components of a wireless phone can include the paramagnetic material which counteracts the electromagnetic radiation emitted by the components of the wireless phone. Alternatively, the paramagnetic material can be formed in a disk-shaped, layered product that includes an outer layer, one or more layers of the paramagnetic material, and an adhesive layer that adheres to the wireless phone.

Figure 11:
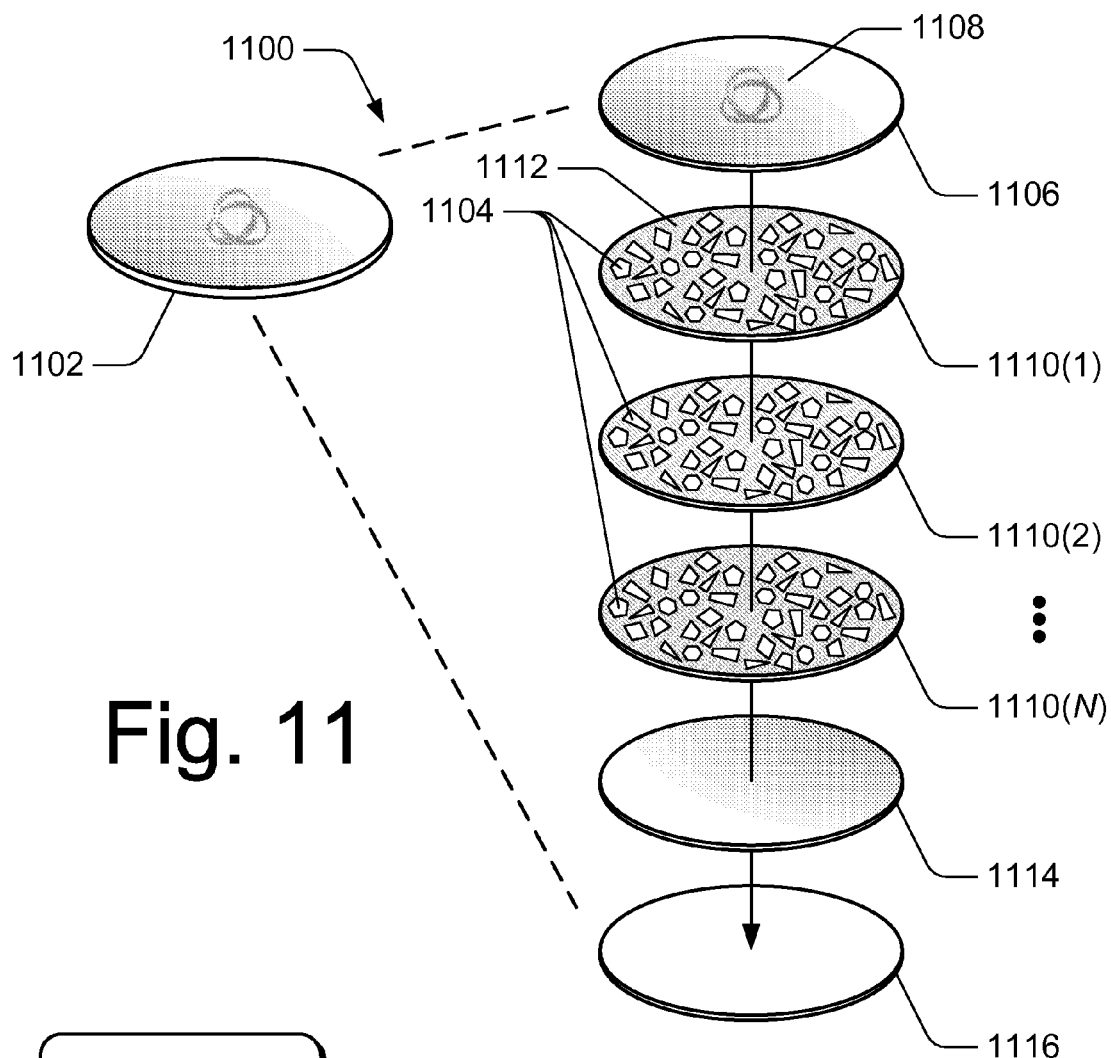
FIG. 11 illustrates an example of paramagnetic material implemented for the transformation of electromagnetic radiation emitted from a device.

FIG. 11 illustrates an example 1100 of paramagnetic material implemented for the transformation of electromagnetic radiation emitted from a device, such as a wireless phone, cellular phone, computer device, or any other similar type of device that may emit electromagnetic radiation. In this example, a disk-shaped, layered product ("paramagnetic disk") 1102 includes paramagnetic material 1104. Any other shape or design of an apparatus that includes paramagnetic material is contemplated.

The paramagnetic disk 1102 in this example is implemented with various layers of different materials. An outer layer 1106 (e.g., a first side, top layer, or top section) is a product apex that can be implemented to include a holographic image or other marketing identifier 1108. The paramagnetic disk 1102 can also include any number of layers 1110(1-N) that are each a layer of paramagnetic material (e.g., activated rare earth elements). In an embodiment, the paramagnetic disk 1102 includes three (3) layers of the paramagnetic material 1104. In alternate embodiments, any number of layers of the paramagnetic material can be utilized to increase, decrease, alter, and/or transform the effects of electromagnetic radiation from an electronic or computing-based device, such as a cell phone for example. In addition, the layers of paramagnetic material 1110(1-N) can each include a base material 1112 to support the paramagnetic material 1104. In various embodiments, the base material 1112 can be an ink-based material, a silica-based material, or other type of material that supports mixing with the paramagnetic material.

The paramagnetic disk 1102 also includes a bonding agent 1112 that bonds the layers of paramagnetic material 1110(1-N) between the outer layer 1106 and an adhesive layer 1114. The adhesive layer 114 (e.g., a second side, bottom layer, or bottom section) can be implemented as a pressure sensitive backing material that can be used to adhere the paramagnetic disk 1102 to a device that emits electromagnetic radiation.

Figure 12:
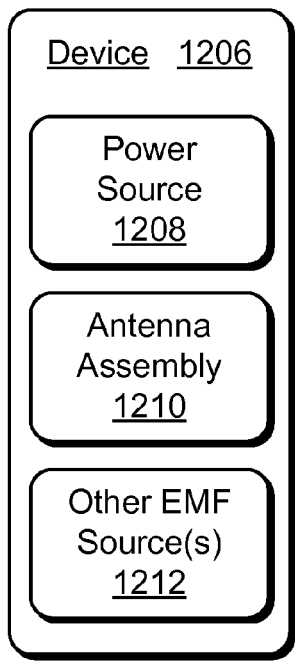
FIG. 12 illustrates an example of a device that emits electromagnetic radiation having paramagnetic material implemented for the transformation of the electromagnetic radiation.
Figure 12:
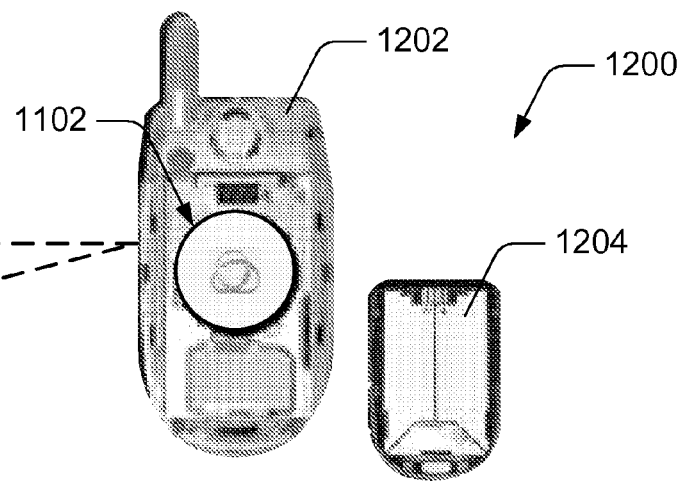

FIG. 12 illustrates a cellular phone 1200 in which an example of the paramagnetic disk 1102 is installed within the housing 1202 of the cell phone 1200 when the battery and/or back plate 1204 of the cell phone is removed. Because cell phones often have quite a rough existence as a portable item, implementing the paramagnetic disk 1102 as a flat, adhesive product is practical and effective. This embodiment provides that the paramagnetic disk 1102 can be positioned inside of the cell phone 1200 against the inner housing 1202 with the battery removed to protect it from damage. As such, the battery can then be removed and/or replaced while the paramagnetic disk 1102 remains in position. Additionally, the flat, adhesive paramagnetic disk 1102 combines a large surface area with a minimum of interference in the handling and usage of the cell phone 1200.

The cell phone 1200 is merely illustrative of the various devices 1206 that may include a power source 1208, an antenna assembly 1210, or any other type of electromagnetic radiation source 1212. The paramagnetic disk 1102 in cell phone 1200 provides the paramagnetic material in a quantity sufficient to counteract the electromagnetic radiation emitted by any one or combination of the sources. In an alternate embodiment, the housing 1202 of the cell phone 1200 is a casing that supports the components of the cell phone, and may be formed to include the paramagnetic material. Other types of devices 1206 that can be implemented to include paramagnetic material in a casing of the device, or with a paramagnetic apparatus such as the paramagnetic disk 1102, are a wireless phone, a microwave, a music player, a portable computing device, a desktop computer, a television, and other devices as shown and/or described with reference to FIG. 1.

In an embodiment, the paramagnetic material 1104 (also shown as paramagnetic material 102 described with reference to FIG. 1) can be manufactured and/or packaged as a powder blend that has an approximate paramagnetic value over 400 to change the EMF waveform emitted from an electronic or computing-based device, and/or to create a biological response to protect against EMF radiation. The paramagnetic material does not block or absorb EMF radiation from a device in as much as it retunes the EMF frequencies, counteracts harmful effects of the electromagnetic radiation, transforms the electromagnetic radiation, and/or neutralizes the electromagnetic radiation.

In various embodiments, the paramagnetic material can transform the electromagnetic radiation to effectuate a desired frequency range of the electromagnetic radiation. The paramagnetic material may also transform the electromagnetic radiation to decrease an intensity of one or more frequencies of the electromagnetic radiation. The paramagnetic material may also counteract the electromagnetic radiation to effectuate a paramagnetic frequency transformation and/or a diamagnetic frequency transformation. Alternatively, and/or in addition, the paramagnetic material can also be implemented to emit an electromagnetic field to counteract the harmful effects of the electromagnetic radiation.

In an embodiment, the paramagnetic material retunes the EMF frequencies of electronic devices like cell phones and computers to assimilate natural frequencies so that they no longer cause harm to a human body's DNA. The homeopathically enhanced and/or crystalline matrix of the neutralizing material can be mixed with an ink base (or with any other base-type material) to support the finely ground minerals and trace elements of the neutralizing material. Other base-type materials that may be used to mix with the neutralizing material include silica, silicon, and/or a caulking type material.

Experiments have shown that human DNA reacts adversely to incoherent manmade electromagnetic fields emanating from a cell phone while recovering from heat shock. Measurements of the time that it takes for DNA to recover from heat shock exposure to the EMF emitted by cell phones shows that the paramagnetic material (such as in the form of the paramagnetic disk 1102) counteracts the harmful effects of the EMF exposure to human DNA, and allows the DNA to recover from the heat shock.

The natural coherent fields from the Aulterra rock crystals (e.g., the paramagnetic material, Aulterra Rock, Aulterra Powder, and/or Aulterra Neutralizer) harmonize the incoherent EMF from a cell phone and retune them to coherent and natural frequencies that do not cause adverse reactions to living tissue. The human body encounters naturally occurring electromagnetic fields, such as from the Earth itself. However, the naturally occurring electromagnetic fields appear as coherent, smooth wave patterns, whereas man-made electromagnetic frequencies are fuzzy or incoherent. When the paramagnetic material is applied to a cell phone 1200 or similar device 1206, such as the example paramagnetic disk 1102, the emitted EMF is evened out from incoherent to coherent wave patterns.

Figure 13:
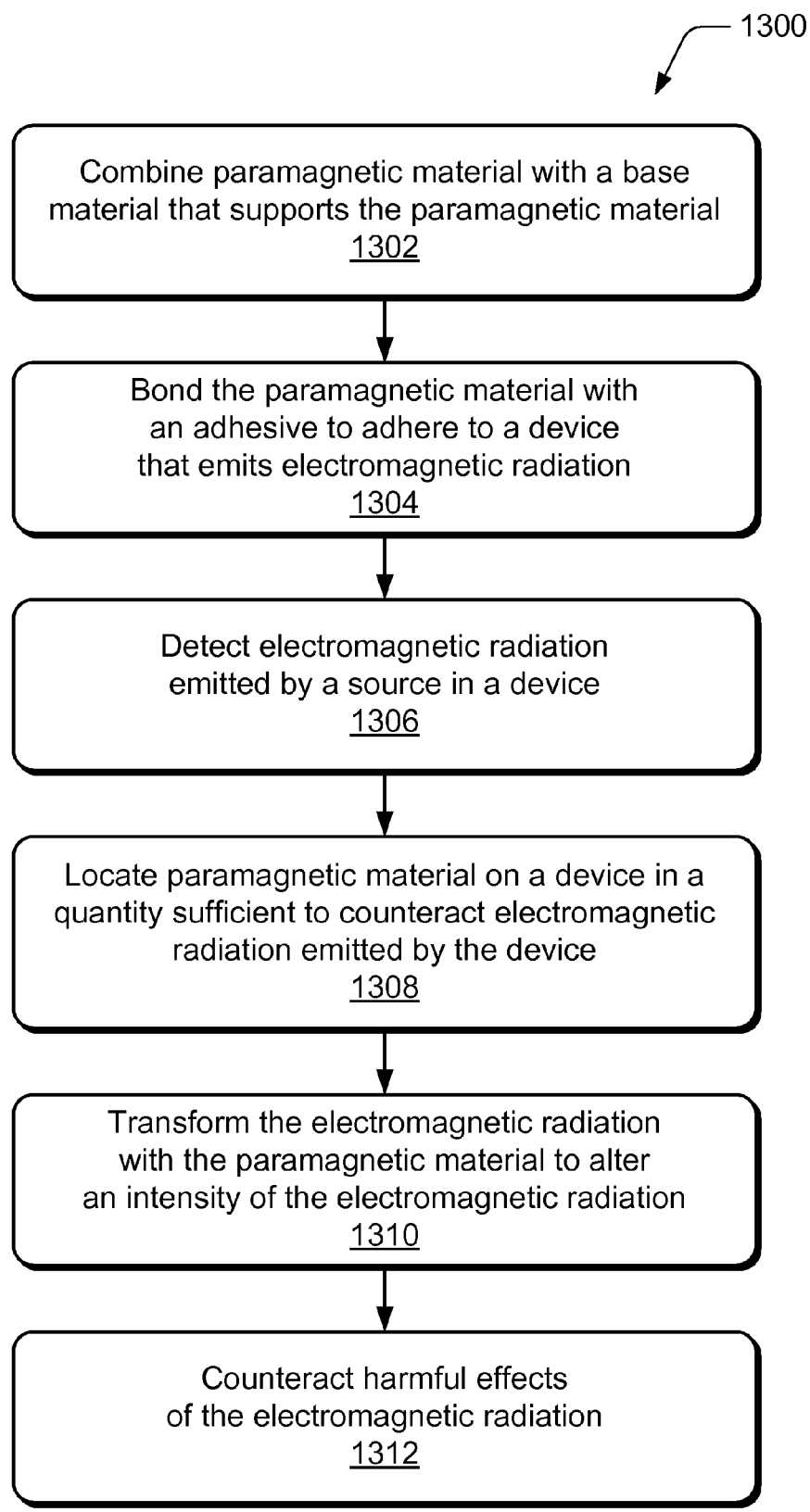
FIG. 13 illustrates example procedure(s) for electromagnetic radiation transformation for powered devices in accordance with one or more embodiments.

FIG. 13 depicts example procedure(s) 1300 of electromagnetic radiation transformation for powered devices, and describes techniques that may be implemented utilizing any environment and/or system described herein. The procedure is shown as a set of blocks and described in an order that is not intended to be construed as a limitation. Any number of the described blocks can be combined in any order to implement the procedure, or an alternate procedure. In this example, reference is made to the paramagnetic material implementation shown in FIG. 11 and the cellular phone device shown in FIG. 12.

Procedure 1300 illustrates an example implementation in which paramagnetic material is located or otherwise disposed on, in, or about a device to counteract electromagnetic radiation emitted by the device. Paramagnetic material can be combined with a base material that supports the paramagnetic material (block 1302). For example, the paramagnetic material 1104 can be combined with a base material 1112 that supports the paramagnetic material 1104 to form the paramagnetic material layers 1110(1-N). The base material 1112 can be an ink-based material or any other base-type material such as silica, silicon, and/or a caulking type material.

The paramagnetic material is bonded with an adhesive to adhere the paramagnetic material to a device that emits electromagnetic radiation (block 1304). For example, the bonding agent 1112 bonds the layers of paramagnetic material 1110(1-N) between the outer layer 1106 and an adhesive layer 1114. Electromagnetic radiation emitted by a source in a device is detected (block 1306). For example, any type of device 1206, such as cell phone 1200, can include a power source 1208, an antenna assembly 1210, or any other type of electromagnetic radiation source 1212.

The intensity of cell phone radiation can be measured using a special type of magnetometer to measure the overall intensity of cell phone radiation across all frequencies (or large portions of the entire spectrum). Cell phone electromagnetic radiation can be measured by placing an antenna, tuned to the frequencies emitted by a cell phone, next to the cell phone that is receiving an active transmission and/or transmitting.

Paramagnetic material is located on (or in) the device in a quantity sufficient to counteract electromagnetic radiation emitted by the device (block 1308). For example, paramagnetic disk 1102 is positioned or located in cellular phone 1200. The electromagnetic radiation (emitted by the device) is transformed with the paramagnetic material to alter an intensity of the electromagnetic radiation (block 1310).

In various implementations, the paramagnetic material emits an electromagnetic field to transform the electromagnetic radiation, the electromagnetic radiation is transformed to effectuate a desired frequency range of the electromagnetic radiation, to alter an intensity or effectuate a decrease in the intensity of one or more frequencies of the electromagnetic radiation, to effectuate a paramagnetic frequency transformation, and/or to effectuate a diamagnetic frequency transformation. Harmful effects of the electromagnetic radiation are then counteracted (block 1312).

Therapeutic Techniques with Paramagnetic Material

As described in the above studies, paramagnetic material may have a variety of therapeutic properties through a variety of different techniques. For example, macroscopic quantum coherence involves the assertion that the energy radiating from paramagnetic material may be highly coherent, e.g., laser-like. This coherence may be used to counteract electromagnetic fields, both internal to a person as well as from external sources. For instance, the coherent energy of the paramagnetic material may be used to influence coherence of other electromagnetic fields. Additionally, the paramagnetic material may also have intrinsic quantum properties, like other complex lattice structures which also exhibit quantum properties.

In another example, a "bio-protective effect" may reduce the intensity of offending electromagnetic radiation. At least two different mechanisms were described for this technique, a biochemical defense response and a physical alteration of encountered electromagnetic radiation, although other mechanisms are also contemplated. In a further example, magneto resistance responses (e.g., Meissner effects) are induced when the paramagnetic material is in the presence of magnetic fields. Thus, paramagnetic shielding (in addition to ferromagnetic shielding) is a likely explanation for the ability of the paramagnetic material to reverse effects of electromagnetic fields, such as on DNA renaturation.

Yet another example involves emission by the paramagnetic material of an electromagnetic field that counteracts electromagnetic fields encountered within that field. This observation was offered as a feasible mechanism to explain how the paramagnetic material 102 (shown in FIG. 1) may cancel detrimental effects of electromagnetic radiation, since it is known that adding coherent information to a classical EMF modifies its ability to influence biological systems. For example, the paramagnetic material may both generate magnetic fields (due to the presence of unpaired electrons) and absorb magnetic fields (a property called magnetic susceptibility). Thus, it is likely that the paramagnetic material also generates a classical EMF which can couple to and counteract another electromagnetic field, such as to neutralize harmful effects to the "other" electromagnetic field. Electromagnetic field emission by the paramagnetic material may also be used to explain the effect of the paramagnetic material to counteract detrimental effects of heavy metals on biological specimens, e.g., DNA. Regardless of the particular mechanism employed, the paramagnetic material may thus provide a wide variety of therapeutic benefits.

Figure 14:
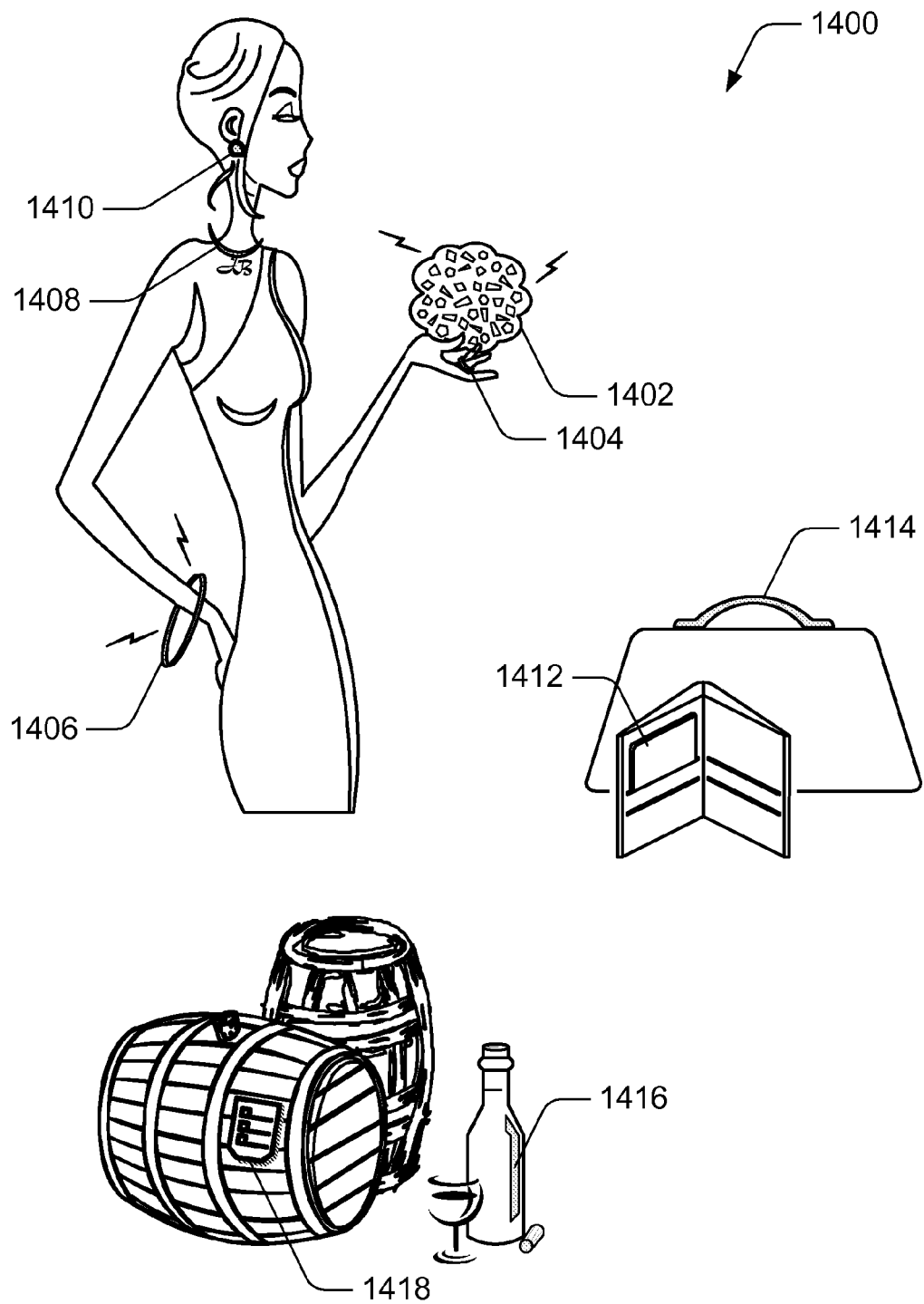
FIG. 14 illustrates examples of paramagnetic material implemented for therapeutic techniques into wearable items for electromagnetic radiation transformation.

To realize these therapeutic benefits, a wide variety of devices may be configured to include paramagnetic material in a quantity sufficient to realize a therapeutic benefit. FIG. 14 illustrates examples 1400 of the paramagnetic material 1402 which may be incorporated for therapeutic techniques within a wide range of items that are carried or worn by a person. For example, jewelry worn by a person can include such items as a ring 1404, a bracelet 1406, a necklace 1408, earrings 1410, eye glasses, and so on.

The paramagnetic material may be also configured within a device that is to be positioned near a person, such as a pillow, in a shape of a credit card 1412 to be placed within a user's wallet, in a handle 1414 of a brief case or purse, and so forth. In such a configuration, it may be desirable to increase the quantity and/or potency of the paramagnetic material over that of paramagnetic material that is placed in contact with a person, such as in the jewelry example above. Thus, the paramagnetic material when so positioned near and/or on a user may provide therapeutic benefits, such as those described in the previous studies.

Although therapeutic uses with a person (i.e., a human being) have been described, the therapeutic uses may be one or a combination of providing a desired effect, having the power to improve or heal, and as being beneficial and/or restorative to an entity, such as an entity as described in relation to FIG. 1. For example, similar therapeutic benefits are expected with other biological organisms, such as household pets (e.g., dogs, cats, and so on). Therefore, use of a paramagnetic material in a sufficient quantity may also be used to protect other biological organisms from electromagnetic radiation, heavy metal toxicity, and so on.

In another example, therapeutic benefits may be realized by perishable products, such as fruit, wine, beer, vegetables, and so on. For instance, a label 1416, 1418 having a therapeutically effective amount of paramagnetic material has been shown to preserve wine for a longer period of time, such as to protect against oxidation and preserve delicate flavors of the wine thereby increasing a shelf life of the wine. A variety of other instances are also contemplated.

Figure 15:
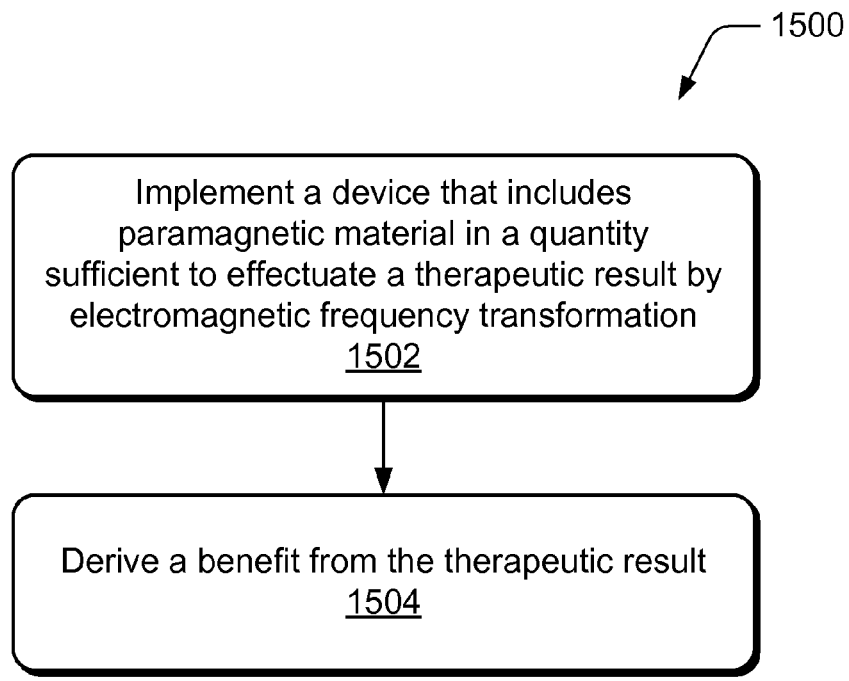
FIG. 15 illustrates example procedure(s) for therapeutic techniques with paramagnetic material in accordance with one or more embodiments.
Figure 16:
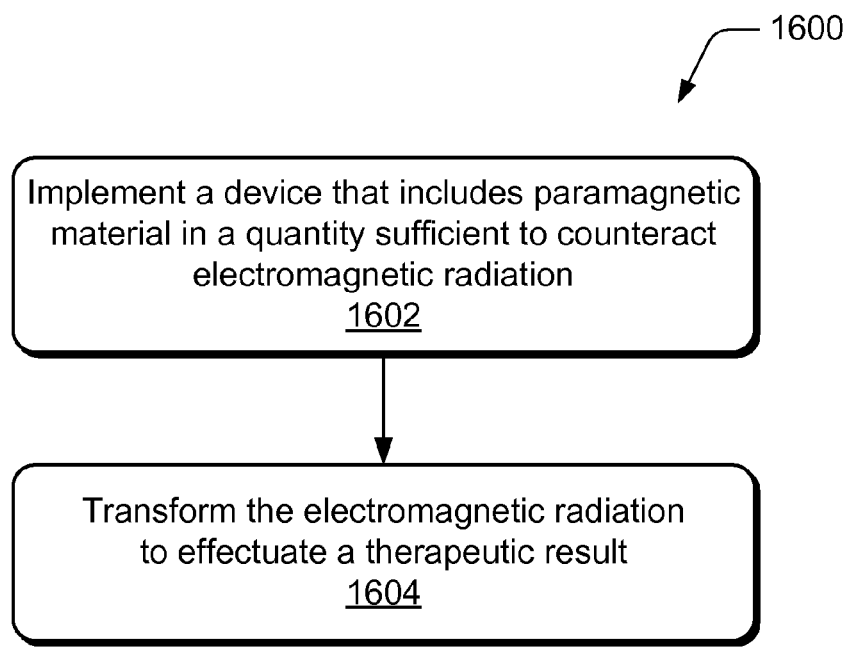
FIG. 16 illustrates example procedure(s) for therapeutic techniques with paramagnetic material in accordance with one or more embodiments.

FIGS. 15 and 16 depict example procedure(s) 1500 and 1600 of therapeutic techniques with paramagnetic material, and describe techniques that may be implemented utilizing any environment and/or system described herein. The procedures are shown as a set of blocks and described in an order that is not intended to be construed as a limitation. Any number of the described blocks can be combined in any order to implement the procedure, or an alternate procedure. In these examples, reference is made to the examples of paramagnetic material implemented for therapeutic techniques as shown in FIG. 14.

Procedure 1500 illustrates an example implementation in which a device is implemented that includes paramagnetic material in a quantity sufficient to derive a beneficial therapeutic result. A device is implemented that includes paramagnetic material in a quantity sufficient to effectuate a therapeutic result by electromagnetic frequency transformation (block 1502). For example, the paramagnetic material may be incorporated within a piece of jewelry, within a label, as a part of a coating, as a powder within a pillow, and so on. Further, the quantity sufficient may be chosen based on proximity to the entity to be protected, size of the entity (e.g., vegetable versus person), and so on. A benefit is then derived from the therapeutic result (block 1504). As previously described, a variety of benefits may be realized, from improved shelf life of wine to health benefits derived from coherence in electromagnetic fields and protection against heavy metal toxicity.

FIG. 16 depicts a procedure 1600 in an exemplary implementation in which a device is implemented having a paramagnetic material to transform electromagnetic radiation to effectuate a therapeutic result. A device is implemented that includes paramagnetic material in a quantity sufficient to counteract electromagnetic radiation (block 1602). This quantity may be determined in a variety of ways. For example, DNA studies previously described showed potential benefits of particular quantities of paramagnetic material in counteracting electromagnetic radiation. The counteracting may also be performed in a variety of ways, such as by altering a waveform of electromagnetic radiation (e.g., coherence), reducing an intensity of electromagnetic radiation at certain frequencies, and so on.

The electromagnetic radiation may then be transformed to effectuate a therapeutic result (block 1604). As previously described, coherence of electromagnetic radiation, reduction in intensity of particular electromagnetic frequencies, and so on may provide a wide range of therapeutic benefits. For instance, heavy metal toxicity may be reduced or eliminated, wine and other perishable items may be given a longer shelf life, DNA may be protected from radiation, and so forth.

Cosmetic Composition with Paramagnetic Material

As previously described, a variety of therapeutic advantages may be realized through the use of the paramagnetic material. Further, these advantages may be implemented using a variety of techniques, such as jewelry and so on as described in the preceding section. In the following embodiments, these advantages are realized through configuration as a cosmetic composition.

Figure 17:
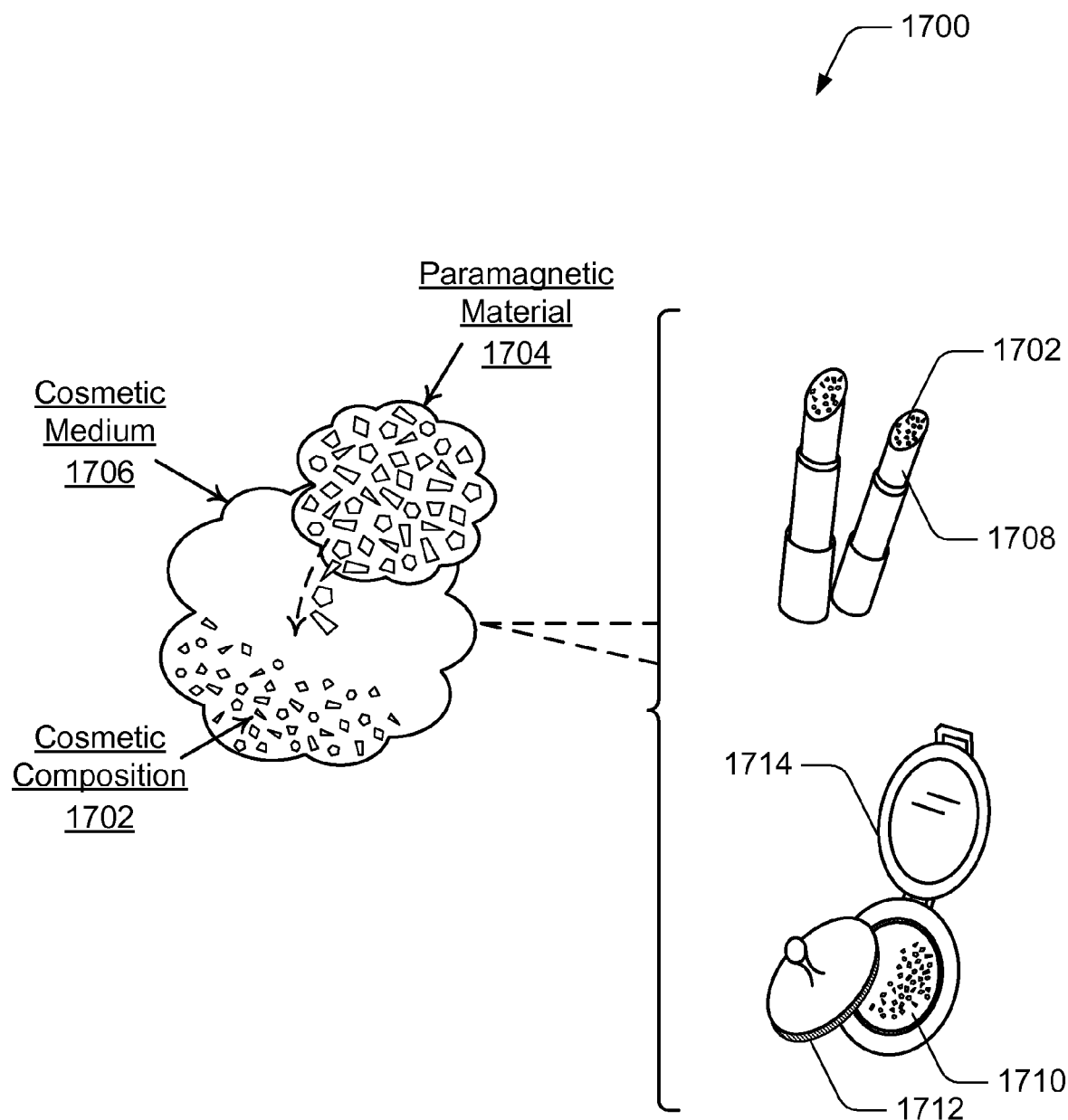
FIG. 17 illustrates examples of paramagnetic material implemented for cosmetic applications to counteract electromagnetic radiation.

FIG. 17 illustrates example implementations 1700 of a cosmetic composition 1702 having a paramagnetic material 1704. The cosmetic composition 1702 includes a cosmetically acceptable medium 1706, such as any medium that is suitable to be applied to the body of a user and may include a variety of lotions, gels, waxes, creams, sprays, powders, masques, shampoos, conditioners, and so on. For example, the cosmetically acceptable medium 1706 may function as a base for a lipstick 1708, eye shadow, blush 1710 (with an applicator 1712 and container 1714 as illustrated), eye liner, and so on. Thus, any one or more of the previously described therapeutic techniques may be realized on the part of a user. Further, these effects may be tailored as desired by a manufacturer.

Figure 18:
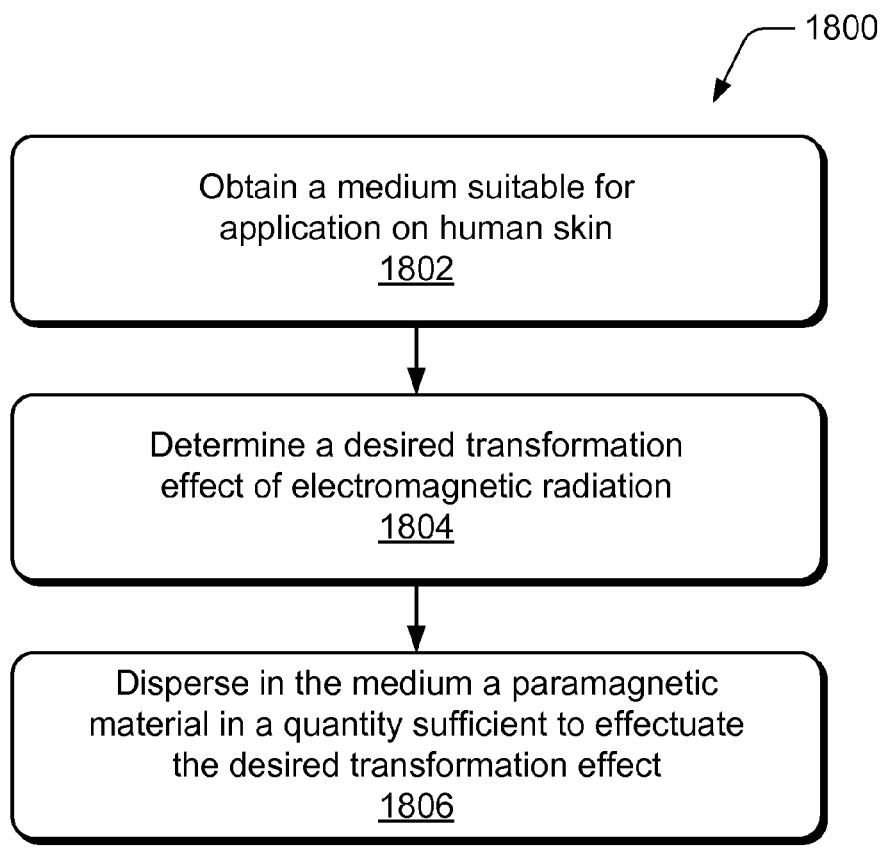
FIG. 18 illustrates example procedure(s) for cosmetic composition with paramagnetic material in accordance with one or more embodiments.
Figure 19:
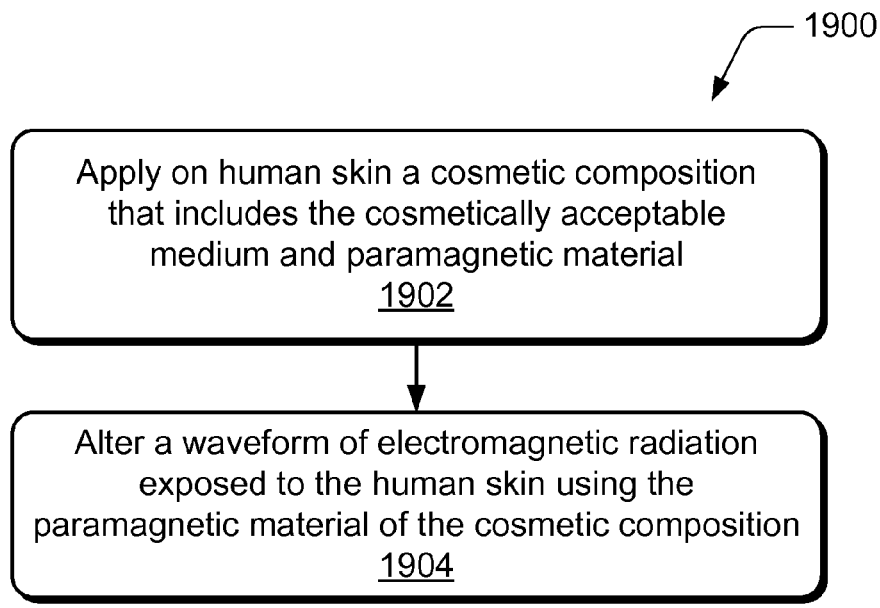
FIG. 19 illustrates example procedure(s) for cosmetic composition with paramagnetic material in accordance with one or more embodiments.

FIGS. 18 and 19 depict example procedure(s) 1800 and 1900 of techniques for cosmetic composition with paramagnetic material, and describe techniques that may be implemented utilizing any environment and/or system described herein. The procedure is shown as a set of blocks and described in an order that is not intended to be construed as a limitation. Any number of the described blocks can be combined in any order to implement the procedure, or an alternate procedure. In this example, reference is made to the examples of paramagnetic material implemented for cosmetic applications as shown in FIG. 17.

Procedure 1800 illustrates an example implementation in which a cosmetic is manufactured to have a desired electromagnetic transformation effect. A medium is obtained that is suitable for application on human skin (block 1802). As previously described, for instance, the medium may be configured for application on a human body, such as on the lips, cheek, eyelids, and so on.

A desired transformation effect of electromagnetic radiation is determined (block 1804). For example, a determination may be made to reduce the effect of external electromagnetic radiation by a certain percentage, e.g., 35 percent, 50 percent, 75 percent, and so on. A variety of other examples are also contemplated, such as to promote coherence of electromagnetic radiation that originates internal to a wearer of the cosmetic, promote a resonance effect to protect DNA, and so forth.

A paramagnetic material is dispersed in the medium in a quantity sufficient to effectuate the desired transformation effect of the electromagnetic radiation (block 1806). Continuing with the previous example, the manufacturer may determine that it is desirable to block approximately 35 percent of electromagnetic radiation encountered by the cosmetic composition, such as that illustrated in the previous DNA studies. Accordingly, the manufacturer may include a quantity sufficient to effectuate this effect in the cosmetically-acceptable medium. A variety of other examples are also contemplated. Therefore, a wearer of the cosmetic composition may realize the advantages of the paramagnetic material, an example of which is further described in the following exemplary procedure.

Procedure 1900 illustrates an example implementation in which a cosmetic composition is applied to human skin. A cosmetic composition comprising a cosmetically acceptable medium having a paramagnetic material is applied on human skin (block 1902). The cosmetic composition, for instance, may be configured as a blush, lotion, lipstick and so on that includes a paramagnetic material, such as the "Aulterra Rock" or "Aulterra Powder" as previously described.

A waveform of electromagnetic radiation exposed to the human skin is altered using the paramagnetic material of the cosmetic composition (block 1904). The paramagnetic material, for instance, may employ a technique that has been referred to as macroscopic quantum coherence. This mechanism includes an assertion that the energy radiating from paramagnetic material may be highly coherent, e.g., laser-like, which may be activated during manufacture of the paramagnetic material 1704 to make the intrinsic energy of the paramagnetic material coherent. The paramagnetic material may also have intrinsic quantum properties, like other complex lattice structures which also exhibit quantum properties. This coherence may operate to apply coherence to other incoherent electromagnetic radiation encountered by the cosmetic composition, thereby making available the previously described therapeutic benefits. A variety of other examples are also contemplated.

Electromagnetic Radiation Transformation for Power Transports

Embodiments of electromagnetic radiation transformation for power transports can include devices, systems, and/or procedures that may utilize paramagnetic and/or diamagnetic techniques to transform electromagnetic frequencies (e.g., radio frequencies), electromagnetic interference or fields, and/or electro-pollution all which may be commonly referred to as electromagnetic radiation, "EMF", or "EMF radiation".

In various embodiments, a power conducting system can include a power transport such as a conduit, power line, electrical cord, and the like that conducts power which is a source of electromagnetic radiation. The power conducting system can also include a paramagnetic material in a quantity sufficient to counteract the electromagnetic radiation emitted by the source. In an embodiment, the power transport can be covered by a coating and/or an insulation cover that includes the paramagnetic material. To counteract harmful effects of the electromagnetic radiation, the paramagnetic material can transform the electromagnetic radiation, such as to effectuate a frequency transformation and/or to alter an intensity or waveform of the electromagnetic radiation.

Figure 20:
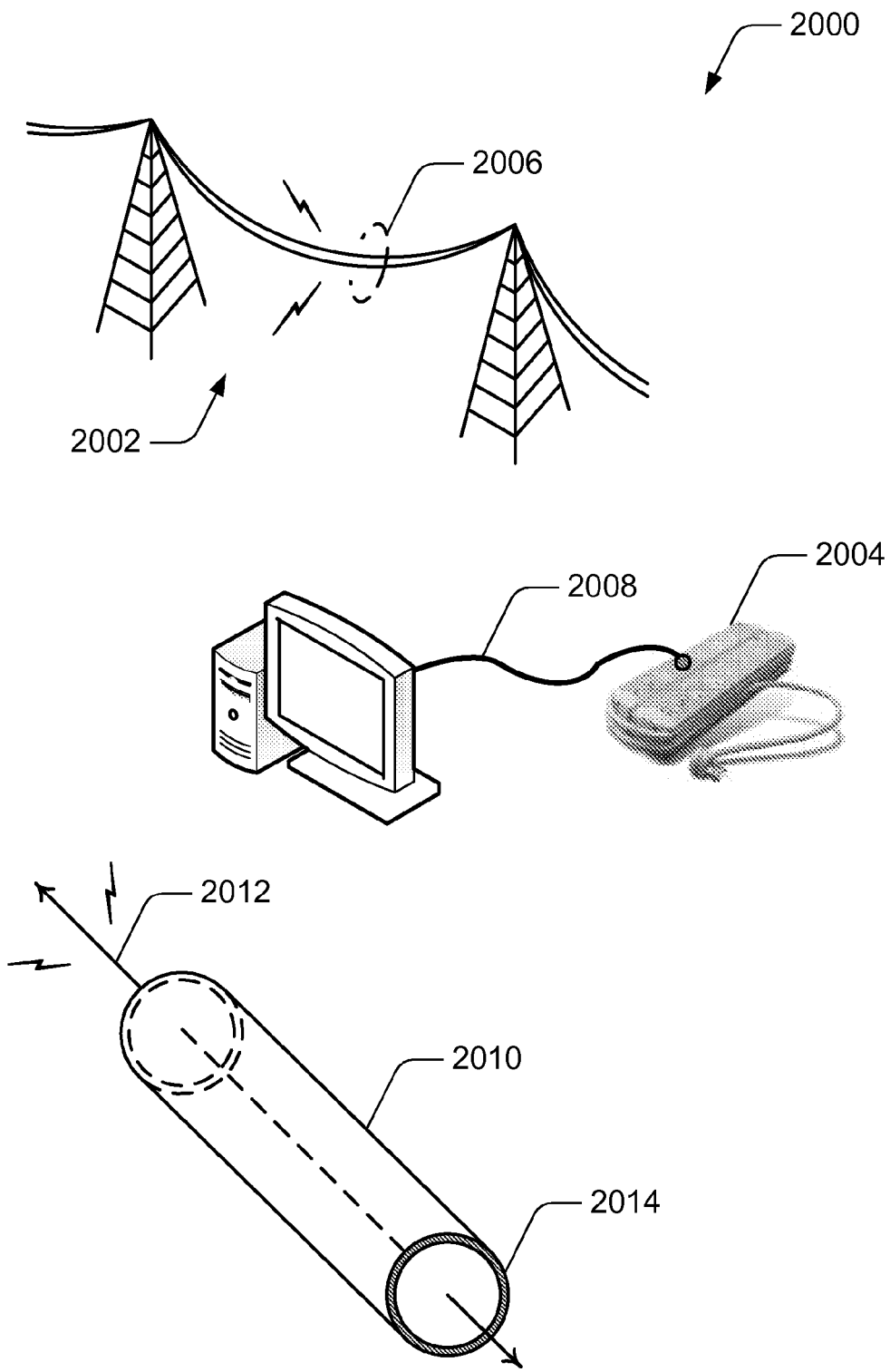
FIG. 20 illustrates examples of paramagnetic material implemented to counteract electromagnetic radiation emitted from power transports.

FIG. 20 illustrates examples 2000 of paramagnetic material which can be implemented for the transformation of electromagnetic radiation emitted from a power conducting system, such as a power line system 2002, a surge protector 2004, and the like. A power transport, such as a power line 2006, a wire or system of wires 2008 (e.g., a power cord, high voltage conductor, power line, and the like), or a conduit 2010 that conducts power 2112 which is a source of electromagnetic radiation.

Any of the power transports (e.g., power line 2006, power cord 2008, or conduit 2010) can have a coating or insulation cover 2014 that includes paramagnetic material in a quantity sufficient to counteract the electromagnetic radiation emitted by the source. A coating or cover 2014 can include a bonding agent that bonds the paramagnetic material with the coating or insulation cover for application on, over, and/or around a power transport.

In various embodiments, the paramagnetic material implemented in a coating or insulation cover can transform the electromagnetic radiation to effectuate a desired frequency range of the electromagnetic radiation. The paramagnetic material may also transform the electromagnetic radiation to decrease an intensity of one or more frequencies of the electromagnetic radiation. The paramagnetic material may also counteract the electromagnetic radiation to effectuate a paramagnetic frequency transformation and/or a diamagnetic frequency transformation. Alternatively, and/or in addition, the paramagnetic material can also be implemented to emit an electromagnetic field to counteract the harmful effects of the electromagnetic radiation.

Figure 21:
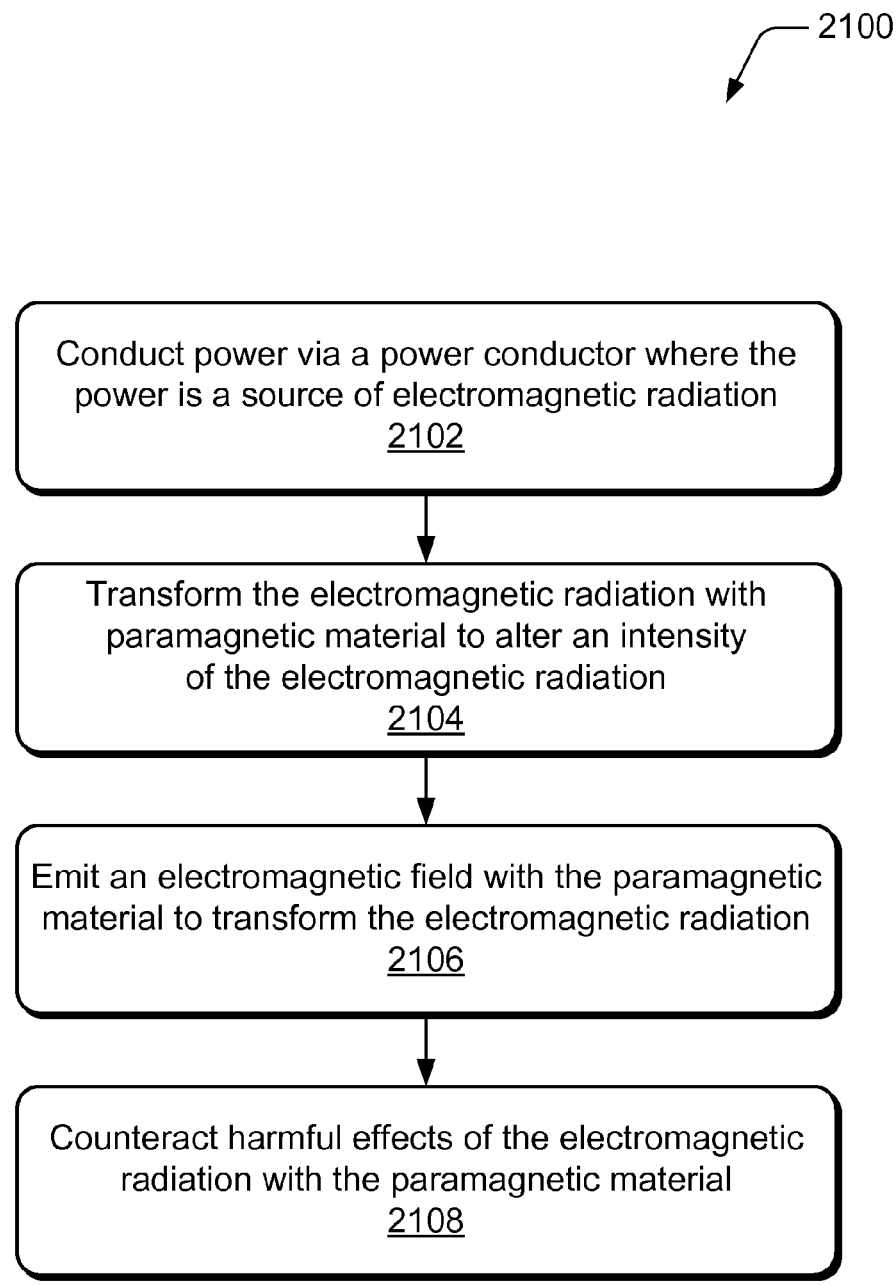
FIG. 21 illustrates example procedure(s) for electromagnetic radiation transformation for power transports in accordance with one or more embodiments.

FIG. 21 depicts example procedure(s) 2100 of electromagnetic radiation transformation for power transports, and describes techniques that may be implemented utilizing any environment and/or system described herein. The procedure is shown as a set of blocks and described in an order that is not intended to be construed as a limitation. Any number of the described blocks can be combined in any order to implement the procedure, or an alternate procedure. In this example, reference is made to the paramagnetic material implementations shown in FIG. 20.

Procedure 2100 illustrates an example implementation in which paramagnetic material is implemented to counteract electromagnetic radiation emitted from a power transport that conducts power which is a source of the electromagnetic radiation. Power is conducted via a power conductor where the power is a source of electromagnetic radiation (block 2102). The electromagnetic radiation is transformed with paramagnetic material to alter an intensity of the electromagnetic radiation (block 2104).

In various implementations, the paramagnetic material emits an electromagnetic field to transform the electromagnetic radiation (block 2106), the electromagnetic radiation is transformed to effectuate a desired frequency range of the electromagnetic radiation, to alter an intensity or effectuate a decrease in the intensity of one or more frequencies of the electromagnetic radiation, to effectuate a paramagnetic frequency transformation, and/or to effectuate a diamagnetic frequency transformation. Harmful effects of the electromagnetic radiation are then contracted with the paramagnetic material (block 2108).

Although embodiments of electromagnetic radiation transformation have been described in language specific to features and/or methods, it is to be understood that the subject of the appended claims is not necessarily limited to the specific features or methods described. Rather, the specific features and methods are disclosed as example implementations of electromagnetic radiation transformation.

The invention claimed is:

1. A wireless phone, comprising:
   a source that emits electromagnetic radiation; and
   a paramagnetic material in a quantity sufficient to counteract the electromagnetic radiation emitted by the source.

2. A wireless phone as recited in claim 1, wherein the wireless phone is a cellular phone configured for cellular communication.

3. A wireless phone as recited in claim 1, further comprising a casing configured to support components of the wireless phone, the casing including the paramagnetic material to counteract the electromagnetic radiation emitted by the components of the wireless phone.

4. A wireless phone as recited in claim 1, further comprising a layered product configured to include the paramagnetic material, the layered product comprising:
   an outer layer;
   one or more layers of the paramagnetic material;
   an adhesive layer configured to adhere to the wireless phone; and
   a bonding agent configured to bond the one or more layers of the paramagnetic material between the outer layer and the adhesive layer.

5. A wireless phone as recited in claim 4, wherein the layered product is a disk-shaped product.

6. A wireless phone as recited in claim 4, wherein the one or more layers of the paramagnetic material each include a base material to support the paramagnetic material.

7. A wireless phone as recited in claim 6, wherein the base material is an ink-based material.

8. A wireless phone as recited in claim 6, wherein the base material is a silica-based material.

9. A wireless phone as recited in claim 1, wherein the paramagnetic material counteracts harmful effects of the electromagnetic radiation.

10. A wireless phone as recited in claim 1, wherein the paramagnetic material transforms the electromagnetic radiation to counteract the electromagnetic radiation.

11. A wireless phone as recited in claim 10, wherein the paramagnetic material transforms the electromagnetic radiation to effectuate a desired frequency range of the electromagnetic radiation.

12. A wireless phone as recited in claim 10, wherein the paramagnetic material transforms the electromagnetic radiation to decrease an intensity of one or more frequencies of the electromagnetic radiation.

13. A wireless phone as recited in claim 1, wherein the paramagnetic material counteracts the electromagnetic radiation to effectuate a paramagnetic frequency transformation.

14. A wireless phone as recited in claim 1, wherein the paramagnetic material counteracts the electromagnetic radiation to effectuate a diamagnetic frequency transformation.

15. A wireless phone as recited in claim 1, wherein the source is an internal power supply that emits the electromagnetic radiation.

16. A wireless phone as recited in claim 1, wherein the source is an antenna system that emits the electromagnetic radiation.

17. A device comprising at least cellular communication functionality, the device comprising:
   a source that emits electromagnetic radiation;
   a paramagnetic material configured to transform the electromagnetic radiation emitted by the source.

18. A device as recited in claim 17, wherein the paramagnetic material is further configured to counteract harmful effects of the electromagnetic radiation.

19. A device as recited in claim 17, wherein the paramagnetic material is further configured to emit an electromagnetic field to counteract harmful effects of the electromagnetic radiation.

20. A device as recited in claim 17, wherein the paramagnetic material transforms the electromagnetic radiation to counteract the electromagnetic radiation.

21. A device as recited in claim 17, wherein the paramagnetic material transforms the electromagnetic radiation to effectuate a desired frequency range of the electromagnetic radiation.

22. A device as recited in claim 17, wherein the paramagnetic material transforms the electromagnetic radiation to decrease an intensity of one or more frequencies of the electromagnetic radiation.

23. A device as recited in claim 17, wherein the paramagnetic material transforms the electromagnetic radiation to effectuate a paramagnetic frequency transformation.

24. A device as recited in claim 17, wherein the paramagnetic material transforms the electromagnetic radiation to effectuate a diamagnetic frequency transformation.

25. A device as recited in claim 17, wherein the source is an internal power supply that emits the electromagnetic radiation.

26. A device as recited in claim 17, wherein the source is an antenna system that emits the electromagnetic radiation.

27. A device as recited in claim 17, further comprising a layered product configured to include the paramagnetic material, the layered product comprising:
an outer layer;
at least one layer of the paramagnetic material;
an adhesive layer configured to adhere to the device; and
a bonding agent configured to bond the at least one layer of paramagnetic material between the outer layer and the adhesive layer.

28. A device as recited in claim 27, wherein the layered product is a disk-shaped product.

29. A device as recited in claim 27, wherein the at least one of layer of the paramagnetic material includes a base material to support the paramagnetic material.

30. A device as recited in claim 29, wherein the base material is an ink-based material.

31. A wireless phone as recited in claim 29, wherein the base material is a silica-based material.

32. A method, comprising:
locating paramagnetic material on a wireless phone in a quantity sufficient to counteract electromagnetic radiation emitted by the wireless phone; and
transforming the electromagnetic radiation with the paramagnetic material to alter an intensity of the electromagnetic radiation.

33. A method as recited in claim 32, wherein transforming the electromagnetic radiation with the paramagnetic material alters the intensity of one or more frequencies of the electromagnetic radiation.

34. A method as recited in claim 32, further comprising counteracting harmful effects of the electromagnetic radiation.

35. A method as recited in claim 32, wherein the paramagnetic material emits an electromagnetic field to transform the electromagnetic radiation.

36. A method as recited in claim 32, further comprising detecting the electromagnetic radiation emitted by an internal power supply of the wireless phone.

37. A method as recited in claim 32, further comprising detecting the electromagnetic radiation emitted by an antenna assembly of the wireless phone.

38. A method as recited in claim 32, further comprising:
combining the paramagnetic material with a base material that supports the paramagnetic material to form at least one layer of the paramagnetic material; and
bonding the at least one layer of the paramagnetic material with an adhesive layer that adheres the at least one layer of the paramagnetic material to the wireless phone.

39. A method as recited in claim 38, wherein the base material that supports the paramagnetic material is at least one of an ink-based material or a silica-based material.

40. A method as recited in claim 32, wherein the electromagnetic radiation is transformed to effectuate a desired frequency range of the electromagnetic radiation.

41. A method as recited in claim 32, wherein the electromagnetic radiation is transformed to effectuate a decrease in the intensity of one or more frequencies of the electromagnetic radiation.

42. A method as recited in claim 32, wherein the electromagnetic radiation is transformed to effectuate a paramagnetic frequency transformation.

43. A method as recited in claim 32, wherein the electromagnetic radiation is transformed to effectuate a diamagnetic frequency transformation.

* * * * *